US010322282B2

(12) United States Patent
Wei et al.

(10) Patent No.: US 10,322,282 B2
(45) Date of Patent: Jun. 18, 2019

(54) EXTERNAL STIMULATION THERAPY FOR DORSAL GENITAL NERVE STIMULATION

(71) Applicant: Medtronic, Inc., Minneapolis, MN (US)

(72) Inventors: Xuan K. Wei, Minnetonka, MN (US); Eric H. Bonde, Minnetonka, MN (US); John R. LaLonde, Lake Elmo, MN (US); David A. Dinsmoor, St. Paul, MN (US)

(73) Assignee: MEDTRONIC, INC., Minneapolis, MN (US)

(*) Notice: Subject to any disclaimer, the term of this patent is extended or adjusted under 35 U.S.C. 154(b) by 863 days.

(21) Appl. No.: 14/731,664

(22) Filed: Jun. 5, 2015

(65) Prior Publication Data

US 2015/0352357 A1 Dec. 10, 2015

Related U.S. Application Data

(60) Provisional application No. 62/008,910, filed on Jun. 6, 2014.

(51) Int. Cl.
*A61N 1/36* (2006.01)
*A61F 13/15* (2006.01)
*A61N 1/04* (2006.01)
*A61F 13/84* (2006.01)
*A61F 13/42* (2006.01)

(52) U.S. Cl.
CPC ....... *A61N 1/36007* (2013.01); *A61N 1/0456* (2013.01); *A61N 1/36014* (2013.01); *A61F 13/42* (2013.01); *A61F 13/84* (2013.01); *A61F 2013/424* (2013.01); *A61F 2013/8479* (2013.01)

(58) Field of Classification Search
CPC . A61N 1/36007; A61F 13/84; A61F 13/8479; A61F 13/42; A61F 13/424
See application file for complete search history.

(56) References Cited

U.S. PATENT DOCUMENTS

| | | | |
|---|---|---|---|
| 4,911,149 A | 3/1990 | Borodulin et al. | |
| 5,571,118 A | 11/1996 | Boutos | |
| 6,436,029 B1 | 8/2002 | Benderev | |
| 6,964,643 B2 | 11/2005 | Hovland et al. | |
| 7,341,579 B2* | 3/2008 | Kinoshita | A61F 13/4753 604/385.03 |
| 7,855,653 B2 | 12/2010 | Rondoni et al. | |
| 7,967,740 B2 | 6/2011 | Mertens et al. | |

(Continued)

OTHER PUBLICATIONS von der Heide, et al., "Effect on muscles on mechanical vibrations produced by the WBV in combination with physical theraphy in treating female stress urinary incontinence," Department of Gynecology and Obstetrics, accessed prior to Nov. 9, 2012, 2 pp.

(Continued)

*Primary Examiner* — Bradley H Philips
(74) *Attorney, Agent, or Firm* — Patterson Thuente Pedersen, P.A.

(57) ABSTRACT

A system including a stimulation generator configured to delivery external stimulation to control or alleviate urinary or fecal incontinence. The system may also include sense electrodes configured to sense the presence of wetness. The system may provide closed loop therapy based on the presence of wetness.

13 Claims, 11 Drawing Sheets

(56) References Cited

U.S. PATENT DOCUMENTS

| | | | |
|---|---|---|---|
| 8,000,792 B1 * | 8/2011 | Dechev | A61N 1/24 |
| | | | 607/138 |
| 8,467,875 B2 | 6/2013 | Bennett et al. | |
| 8,684,008 B2 | 4/2014 | St. Anne | |
| 2007/0150034 A1 * | 6/2007 | Rooney | A61N 1/0531 |
| | | | 607/115 |
| 2007/0239224 A1 * | 10/2007 | Bennett | A61N 1/0524 |
| | | | 607/41 |
| 2007/0252714 A1 * | 11/2007 | Rondoni | A61B 5/0002 |
| | | | 340/573.5 |
| 2009/0000571 A1 | 1/2009 | Podrazhansky et al. | |
| 2015/0290450 A1 * | 10/2015 | Kolb | A61N 1/0452 |
| | | | 607/41 |

OTHER PUBLICATIONS

"How intone works to stop female bladder leakage," InControl Medical, last accessed prior to Nov. 9, 2012, from https://www.incontrolmedical.com/, 4 pp.

"Transcutaneous Mechanical Nerve Stimulator (TMNS) User's Guide," Orion Medical Group, Inc., retrieved on May 16, 2014 from www.medicalvibrator.com, 11 pp.

Sonksen, et al., "Transcutaneous Mechanical Nerve Stimulation Using Perineal Vibration: A Novel Method for the Treatment of Female Stress Urinary Incontinence," The Journal of Urology, vol. 178, Nov. 2007, pp. 2025-2058.

\* cited by examiner

EXTERNAL STIMULATION THERAPY FOR DORSAL GENITAL NERVE STIMULATION

This application claims the benefit of U.S. Provisional Application Ser. No. 62/008,910 by Xuan K. Wei at al., which was filed on Jun. 6, 2014, and is entitled "EXTERNAL STIMULATION THEARPY FOR DORSAL GENITAL NERVE STIMULATION." U.S. Provisional Application Ser. No. 62/008,910 by Xuan K. Wei at al. is incorporated herein by reference in its entirety.

TECHNICAL FIELD

The disclosure relates to external delivery of stimulation therapy by a medical device.

BACKGROUND

Medical therapy may be delivered to alleviate a variety of pelvic floor disorders, such as dysfunction relating to urinary or fecal voiding. Examples of urinary voiding dysfunction include urge and stress incontinence. Examples of fecal voiding dysfunction include fecal incontinence. Pelvic floor disorders may afflict people of all ages, genders, and races, and may be associated with aging, injury or illness. In some cases, muscles, nerves, organs, and/or conduits within the pelvic floor that cooperate to support urinary or fecal voiding function may become dysfunctional. Stimulation therapy may be effective in eliminating or reducing the severity of symptoms of such dysfunction, such as urinary or fecal incontinence.

SUMMARY

In general, the disclosure is directed to systems and method for delivering external electrical stimulation to a dorsal genital nerve (DGN) of a patient.

In one example, the disclosure is directed to an external device for stimulation of a dorsal genital nerve. The external device comprises a stimulation generator configured to generate stimulation for stimulation of a first dorsal genital nerve and a second dorsal genital nerve of a patient; and at least two stimulation electrodes positioned to deliver the stimulation to the first dorsal genital nerve and the second dorsal genital nerve. In some examples, the external device also includes at least two sensing electrodes and sensing circuitry configured to sense urine leakage via the sensing electrodes.

In another example, the disclosure is directed to a method comprising sensing wetness caused by urine leakage; generating stimulation configured to stimulate a first dorsal genital nerve and a second dorsal genital nerve of a patient in response to the sensed wetness; and delivering, via at least two external stimulation electrodes, the stimulation to the first dorsal genital nerve and the second dorsal genital nerve.

In another example, the disclosure is directed to an external stimulating device comprising means for generating stimulation for stimulation of a first dorsal genital nerve and a second dorsal genital nerve of a patient; and means for delivering the stimulation to the first dorsal genital nerve and the second dorsal genital nerves.

DETAILED DESCRIPTION

Figure 1:
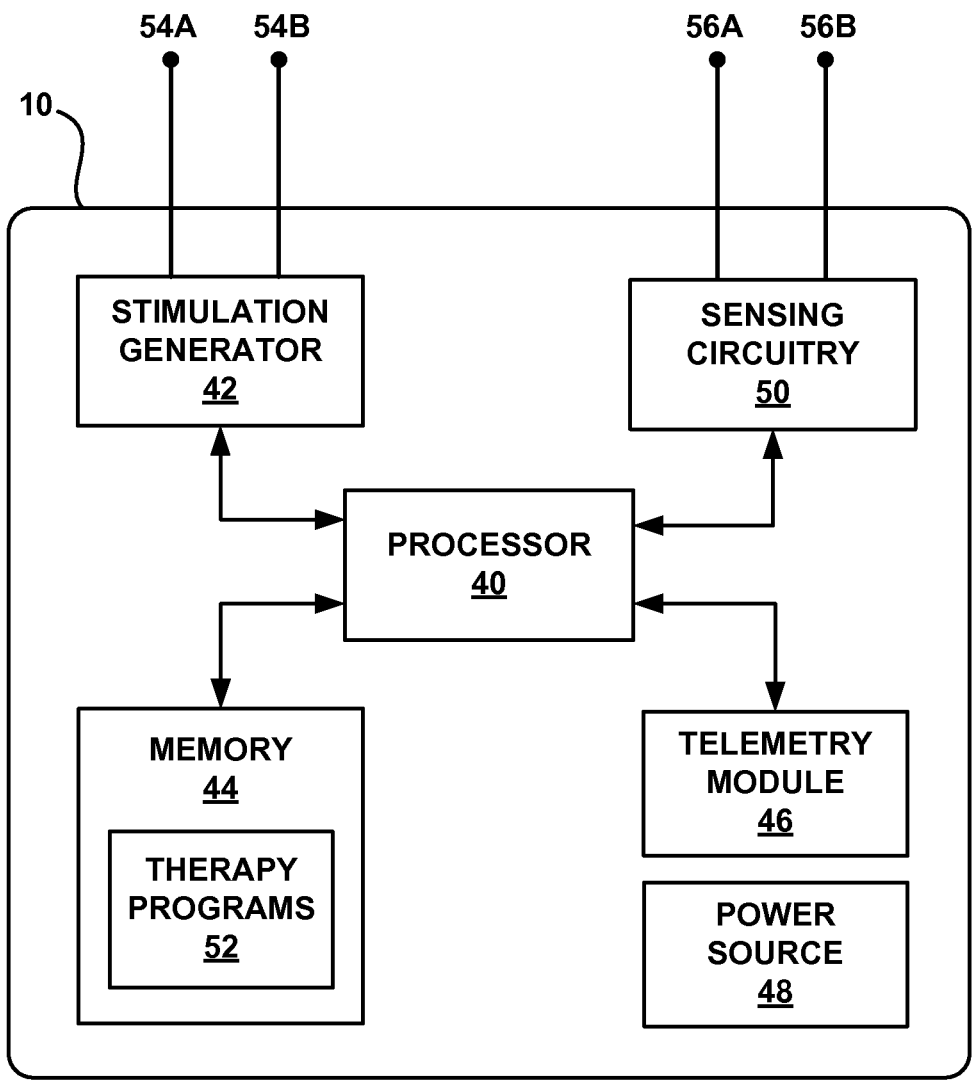
FIG. 1 is a block diagram illustrating an example medical device configured to deliver external dorsal genital nerve (DGN) stimulation to alleviate pelvic floor dysfunction.

The devices, systems, and techniques described herein may be useful for delivering external stimulation to at least one DGN of a medical patient to alleviate one or more pelvic floor disorders, such as urinary or fecal voiding dysfunction. Examples of urinary or fecal voiding dysfunction include urge incontinence, stress incontinence and fecal incontinence.

In accordance with examples of this disclosure, a stimulator is configured to provide external stimulation of the Dorsal Genital Nerve (DGN) of a medical patient. The stimulation may be electrical stimulation, mechanical stimulation, or a combination of both. In some examples, the stimulation may be intermittent. For example, the stimulation need not be delivered continuously and instead may be delivered in response to user input, at various times and/or in response to sensed events, such as leakage. A leakage event may include, for example, the unwanted release of either urine or fecal matter. Alternatively, the stimulation could be delivered on a continuous basis. The stimulator may be an external stimulator and, in some examples, may be self-contained. For example, the external stimulator may be provided as a unitary device that can be affixed to the patient. In other examples, portions of the external stimulator may be provided in separate sub-components that interact with one another via wired or wireless communication.

In some examples, the stimulator may be configured to be temporarily attached to the skin midline in the clitoris area, or slightly above the clitoris, in a female human patient. In other examples, for a male human patient, the stimulator may be configured to be temporarily attached to the shaft of the penis, e.g., near the base of the penis. In either case, the stimulator may be configured to deliver electrical and/or mechanical stimulation to the DGN of the patient externally to alleviate urge incontinence, stress incontinence and/or fecal incontinence.

An external electrical stimulator, in some examples, may have at least two electrodes that are positioned to be in contact with the skin when the stimulator is placed on the patient. The electrical stimulation electrodes may deliver electrical stimulation externally to stimulate the DGN and/or one or more of its branches transcutaneously, i.e., through the skin and without the need to pierce the skin or implant a device within the patient.

For female patients, the stimulator may have at least two electrodes positioned for placement at a midline in the clitoris area or proximate to the clitoris (e.g., in the case of a device having a patch- or pad-like form factor as described below). In some examples, a position proximate to the clitoris may be a position slightly above the clitoris, e.g., where above may be in a direction toward the waist of the patient relative to the clitoris. In some examples, the electrical stimulation electrodes may be positioned for placement on opposite sides of the midline in the clitoris area when the stimulator is attached to the patient. One electrode may form an anode and another electrode may form a cathode for delivery of electrical stimulation current to the skin of the patient. For example, the electrical stimulation current may be sourced by one electrode and sunk by the other electrode. In other examples, three or more electrodes may be used in various combinations to deliver the stimulation to the patient.

Figure 11:
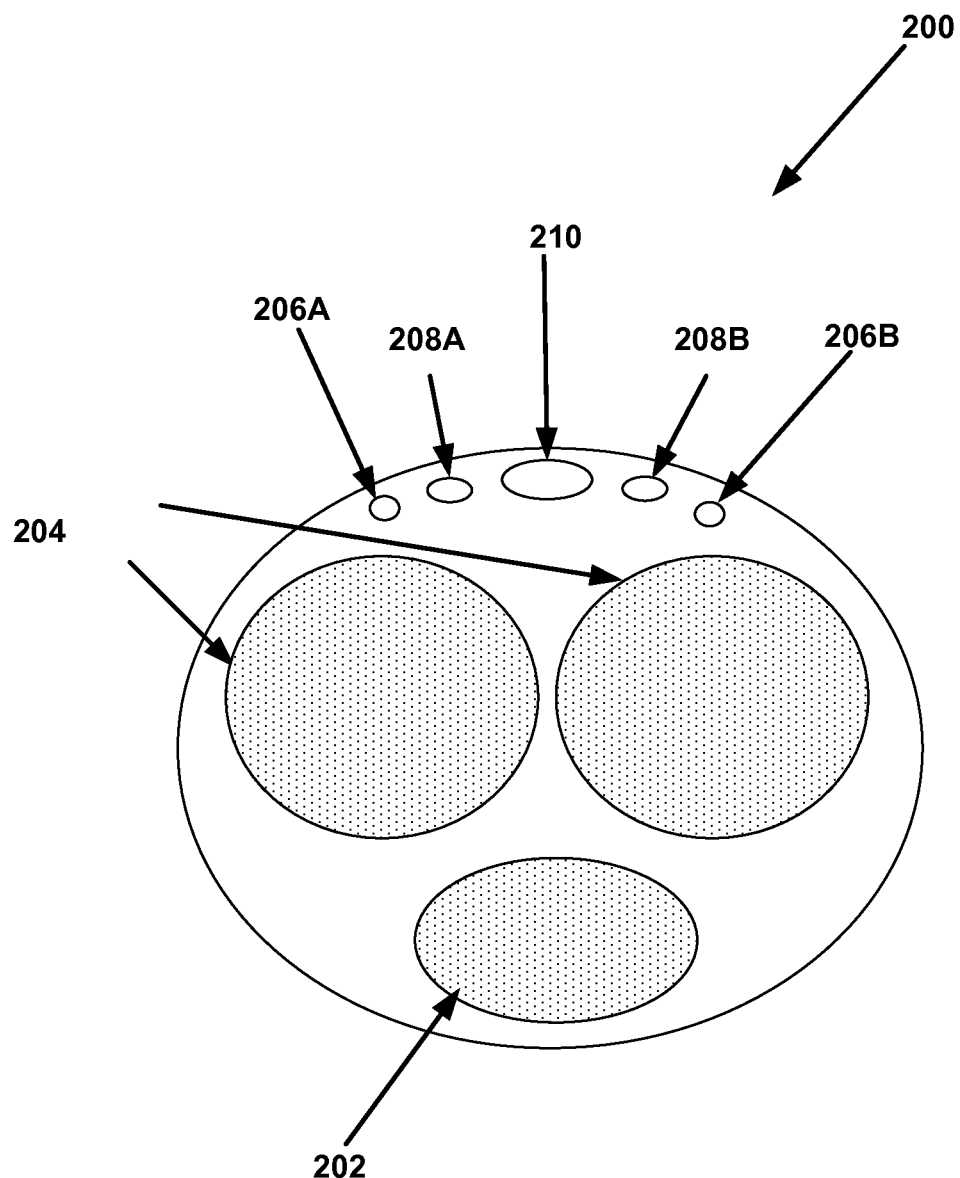
FIG. 11 is a conceptual, cross-sectional view of a human penis, illustrating the DGN relative to other anatomical structure.

For male patients, the external stimulator may have at least two electrodes positioned for placement, e.g., at approximately the 10 and 2 o'clock positions, on the shaft of the penis or near the base of the penis (e.g., in the case of a device having a ring form factor as described below). The 10 and 2 o'clock positions may be viewed on a cross-section of the penis that is transverse to a longitudinal axis of the penis, with the urethra being at approximately 6 o'clock and the dorsal vein being at approximately 12 o'clock in such a cross-section. The electrodes may be positioned to be placed on the side of the penis adjacent the DGN. The DGN tends to be close to the skin surface on the dorsal side of the penis adjacent the corpora cavernosa penis, which is on a side opposite the urethra. As shown in FIG. 11, the DGN is superficial on the dorsal side at approximately 10 o'clock and 2 o'clock on a cross section of the penis. The DGN runs the length of the shaft of the penis until it reaches the glans where it fans out. FIG. 11 is not necessarily anatomically correct, but is provided to illustrate the portions of the anatomy to which the DGN stimulator may be applied.

As an example, for a male patient, the external stimulator may have a ring-like form factor. As in the female patient example above, for a male patient, one stimulation electrode of the device may form an anode and another stimulation electrode may form a cathode for delivery of electrical stimulation current between the electrodes. Again, although two electrodes are described for purposes of illustration, three or more electrodes may be used in various combinations to deliver the stimulation to the patient.

The external stimulator may provide both mechanical and electrical stimulation. Alternatively, in some examples, the stimulator may provide only electrical stimulation or only mechanical stimulation. Accordingly, the stimulator may provide electrical and/or mechanical stimulation. The mechanical stimulation may be vibratory stimulation. For example, the external stimulator may include a vibratory element, such as a piezoelectric element or other vibrating transducer. The two stimulation modalities (i.e., electrical and mechanical) can be performed substantially simultaneously or independently of one another. In some examples, the two stimulation modalities may be delivered in an overlapping manner such that portions of the electrical and mechanical stimulation are delivered simultaneously at some times and independently at other times.

In one example, a power source and electronics for the external stimulator can be housed in a sealed container. In some examples, the stimulator may include a flexible circuit that carries various electronics. In another example, the stimulator may contain embedded chips or electronics on the electrodes or supporting materials that embed the electronics and electrodes. In some examples, the electrodes and electronic circuitry may be integrated with one another. In various examples, the stimulator may contain CMOS-based electronics.

In one example, the stimulator may take the form of a disposable, one-piece, self-contained device including a power source, electronics, and electrodes. In other examples, portions of the external stimulator may be provided in separate sub-components that interact with one another via wired or wireless communication. In some examples, the external stimulator may be reusable and can be attached and detached to a disposable sheath that contains at least two electrodes and is designed to be in direct contact with the skin. In this case, electronics in the stimulator may be in electrical contact with corresponding electrodes, or electrical contacts, carried by the disposable sheath when the stimulator is attached to the sheath, or vice versa. In some examples, the disposable sheath may include a moisture absorbing pad. In some examples, the disposable sheath may include one or more openings through which the electrodes of the external stimulator may extend to make contact with the patient's skin. In some examples, the sheath may enclose the stimulator entirely or substantially. Alternatively, the sheath may be a sheet-like layer that does not enclose the stimulator, but is disposed between the stimulator and the skin of the patient. A built-in gel layer can be provided in such a sheath, which may improve electrode contact with the skin, e.g., without the need for shaving. In some examples, each electrode contact on the sheath may be surrounded by separate gel layer. In other examples, gel may be applied by the patient before each use in order to improve electrode contact.

As an illustration, an external stimulator may be formed with electrical stimulation electrodes (and/or mechanical stimulation elements), associated stimulation and sensing circuitry, and a power source (and optionally telemetry circuitry) within a device housing member. For example, the device housing member may be a material that substantially encapsulates the components of the stimulator but is configured to expose the electrodes or leads carrying the electrodes for delivery of external electrical stimulation. Likewise, the device housing member may expose one or more mechanical stimulator elements or be configured to transmit mechanical stimulation through the housing. The device housing member may be formed with a recess or cavity to contain circuitry components, or be molded, cast or extruded over the circuitry components. Examples of various materials for the device housing member include silicone, polyurethane, liquid crystal polymer, titanium, polyimide or other materials suitable for temporary or prolonged external contact with a patient. Other materials may be used, e.g., if a sheath is provided as an interposing layer between the patient and the device housing member.

A sheath may include complementary stimulation electrodes that are positioned for electrical contact with the respective electrodes exposed by the device housing member to thereby transmit electrical stimulation from the housing to the patient skin surface. When the sheath is properly positioned over the device, the electrodes of the device housing member and the sheath are aligned to contact one another. The complementary electrodes extend through the sheath from the device housing member to contact the skin of the patient. In some examples, the sheath may also include complementary sense electrodes. In this case, the sheath may be a layer that stands between the patient and the device housing member, or a sheath that encloses the device housing member either entirely or substantially. Accordingly, the sheath may form a substantially sheet-like, planar layer or a bag-like or box-like enclosure. Like the device housing member, the sheath may be formed from various materials, including silicone, polyurethane, liquid crystal polymer, titanium or other materials suitable for temporary or prolonged external contact with a patient. In some examples, it may be desirable that the sheath is flexible and/or conformable so as to wrap around the device housing member, and/or so as to promote patient comfort. If the sheath is a sheet-like layer, the sheath may be attached to the device housing member, e.g., with an adhesive, hook-and-loop fastener, snap-fit fastener or press-fit fastener.

In examples wherein the sheath is a moisture absorbing pad, the moisture absorbing pad may include one or more openings through which one or more electrodes may make contact with a patient. For example, a lead including the stimulation electrodes may extend through an opening in the moisture absorbing pad. In some examples, the moisture absorbing pad may include another opening through which sensing electrodes may be exposed. In some examples, the lead and the sensing electrodes may extend through the same opening. The sensing electrodes may be used to sense wetness and/or leakage volumes. In some examples, the moisture absorbing pad is positioned between the sensing electrodes and a patient. The sensing electrodes may sense the presence of wetness and/or leakage volume based on a change of impedance. Sensing of wetness and/or leakage volumes may generally be referred to as sensing of wetness in this disclosure. In this example, the sensing electrodes may include an anode and a cathode used by sensing circuitry to sense electrical impedance (e.g., electrical resistance) between the electrodes, and thereby sense wetness based on the level of the sensed electrical impedance. The impedance of the moisture absorbing pad may change as the amount of liquid absorbed by the pad increases. In some examples, the moisture absorbing pad may be disposable.

The device housing member also may expose components, such as the sensing electrodes and/or the stimulation electrodes. For example, sensing electrodes may protrude at least partially from the device housing member. In some examples, the stimulation electrodes may be positioned on a lead extending from the device housing member. The lead may be configured to allow the stimulation electrodes to provide bilateral stimulation to the patient. For example, stimulation may be provided to both sides of the midline of the patient's body, to the DGN on each side of the midline of the patient. The electrodes may be positioned on a device housing member to be placed on the skin of the patient to either provide stimulation or to sense wetness when the external stimulator is attached to the patient. In some examples, a sheath as described above may include complementary sensing electrodes that are positioned for electrical contact with the respective sensing electrodes exposed by the device housing member to thereby permit impedance measurements to be obtained from the skin surface of the patient by sensing circuitry within the device housing member via the sheath.

To apply electrical and/or mechanical stimulation, the external stimulator is applied, e.g., temporarily attached, to the skin of the patient, either directly or via a sheath, as described above. In some examples, the stimulator may be configured such that stimulation starts automatically, e.g., upon placement of the stimulator on the skin or some other action, and shuts off after a certain period of time, e.g., such as approximately 30 minutes. As one example, placement of the device on the skin may be detected by sense electrodes that sense a change in electrical impedance, and thereby trigger delivery of stimulation. Alternatively, as another example, placement of the device on the skin may be detected by user input, such as pressing a button, entering a command via a remote programmer, or removing an interposing insulator later between a battery and power terminals on the device, e.g., to initially power on the device.

The external stimulator may be configured such that the stimulation starts initially for a period of time, stops after the period of time has elapsed, and then automatically restarts later, e.g., at regular or irregular intervals, to deliver stimulation intermittently. Alternatively, the stimulator may deliver stimulation on a full-time basis, rather than intermittently. In some cases, stimulation may be delivered for a period of time on an on-demand basis, e.g., in response to some action by the patient or a caregiver, such as pressing a button, entering a command, tapping the device, or the like.

Additionally or alternatively, the external stimulator may be configured so that stimulation is delivered in a closed-loop manner in response to sensing of an event, such as the sensing of wetness, a leakage volume, or the like, e.g., via a sensor carried by the external stimulator. For example, upon detection of wetness, stimulation may be delivered for a predetermined period of time, and then stimulation may be stopped after the predetermined period of time has elapsed. The external stimulator may deliver stimulation again the next time that wetness is sensed by the device, or when additional wetness is sensed. In some examples, closed loop stimulation, in response to wetness sensing, may be combined with delivery of stimulation in response to a schedule or in response to patient input. Hence, the external stimulator may be configured to deliver external stimulation in response to placement of the stimulator on the patient, at various times as indicated by a calendar, clock or timer, in response to user input, and/or in response to sensing of wetness.

In some examples, the external stimulator may be configured so that stimulation is delivered in order to train the patient to control incontinence while using less stimulation or without the aid of stimulation. In some examples, a patient may be instructed to perform one or more exercises in response to the delivery of stimulation. The external stimulator may be programmed to slowly increase the intervals between the delivery of stimulation to the patient. In other examples, the external stimulator may be programmed to provide stimulation at predetermined intervals for a first period of time and only in response to sensing an event, such as the sensing of wetness during a second period of time, the first period of time preceding the second period of time.

The electrical stimulation can be delivered as stimulation pulses and performed with stimulation parameters of a pulse rate between approximately 5-0,000 Hz, between about 7-1000 Hz, between about 10-100 Hz, and in some examples, at approximately 14 Hz. The stimulation parameters may also include a pulse width of approximately 30 microseconds to 1 millisecond, and a current amplitude of approximately 0.1-50 milliamps. Mechanical stimulation may be delivered and performed with stimulation parameters of approximately 1 to 500 Hz for frequency, approximately 16 milliseconds to 1 second per cycle, and approximately 0.1 to 10 g's of g-force for amplitude. In some examples with only two stimulation electrodes, electrical stimulation may be provided using alternatingly polarities of the two stimulation electrodes. For example, the polarity of the electrodes may switch on a time-interleaved basis. In examples with at least three electrodes, one electrode may be programmed as an anode and two electrodes may be programmed as cathodes. The two cathode electrodes may be located proximate the branches of the DGN. An anode may be located approximately equidistant from the two cathodes. In some examples, a cycle may refer to a period of time during which mechanical stimulation is delivered, i.e., is ON, between periods of time during which mechanical stimulation is not delivered, i.e., is OFF. In some examples, the mechanical stimulation may take the form of a sine wave. Electrical or mechanical stimulation can be delivered continuously or in a series of bursts, where each burst carries a plurality of stimulation pulses, and there is a period of time between bursts during which no pulses are delivered. In some examples, as discussed above, electrical and mechanical stimulation may be delivered, in terms of time, simultaneously, in a partially overlapping manner, or separately and independently of one another.

Stimulation may be delivered for predetermined intervals of time. As one example, stimulation intervals for electrical stimulation and/or mechanical stimulation may range from 3 times a day to once a week, e.g., for a duration of approximately 5-30 minutes each time. In this example, the stimulation may be delivered automatically at various times, e.g., based on a calendar, clock or timer, as discussed above. As also mentioned above, the intermittent stimulation can be applied on-demand by the patient. For example, the patient may wish to activate stimulation, e.g., by user input, immediately before attending a social event, engaging in exercise, engaging in sexual activities, and/or other activities. The patient may enter a command to start stimulation by interacting with the stimulator or a programmer for the stimulator.

The stimulation may have a lasting effect in alleviating symptoms for some period of time after stimulation is stopped. For example, if a patient engages in exercise, delivery of stimulation before exercise may provide a window of time in which incontinence may be avoided or severity of incontinence may be reduced during exercise. In some cases, the stimulation also may be delivered during the activity, e.g., in response to patient demand or for a period of time after patient demand, or in response to sensed leakage, at an intensity that is sufficient to alleviate symptoms during the activity.

In some examples, as discussed above, an external stimulator as described in this disclosure, may operate on a closed-loop basis in response to sensed events, such as sensed wetness. In this case, the external stimulation may be or form part of a closed-loop, external DGN stimulation system. In a closed-loop DGN stimulation system, the external DGN stimulator may be coupled with one or more sensors, as described above, for detection of wetness and/or leakage in order to deliver stimulation in response to sensing such wetness and/or leakage. For example, the closed-loop, external DGN stimulation system may be configured such that the external stimulation delivers stimulation (e.g., electrical and/or mechanical stimulation) when a first sign of wetness and/or leakage is detected. Also, external DGN stimulation may be delivered continuously or at various intervals if wetness continues to be sensed over time. These different modes for controlling and initiating stimulation may be used individually or together in any combination in a stimulation system as described in this disclosure.

In one example for female patients, the external stimulator in the closed-loop DGN stimulation system may include a closed-loop stimulator patch- or pad-like member having a plurality of electrodes. The patch- or pad-like member may carry sense electrodes, sensing circuitry and stimulation generator circuitry. In some examples, the closed-loop stimulator patch- or pad-like member may have at least four electrodes, including a first set of at least two electrodes positioned on the patch for placement approximately midline in the clitoris area or slightly above the clitoris when the stimulator patch or pad is applied to the patient, and a second set of at least two electrodes positioned on the stimulator patch or pad for placement to straddle the urethra meatus for wetness sensing when the patch or pad is applied to the patient.

In some examples for female patients, the external stimulator may include a reusable portion and a disposable portion. For example, the reusable portion may include all or substantially all of the electrical components, including for example, the stimulation generator and the electrodes. The disposable portion may be a pad-like member, such as a moisture absorbing pad. The moisture absorbing pad may be configured to encapsulate or substantially encapsulate the reusable portion. The moisture absorbing pad may include one or more openings through which the first and/or second set of electrodes access the patient. For example, a lead carrying a set of stimulation electrodes may extend through the moisture absorbing pad.

The first set of at least two electrodes, oriented for placement approximately midline in the clitoris area or slightly above the clitoris, may form electrical stimulation electrodes for delivery of electrical stimulation. The second set of at least two electrodes may form sense electrodes for sensing of wetness. One electrode in the first set may form an anode and another electrode in the second set may form a cathode to deliver electrical current for electrical stimulation. Alternatively, each of the electrodes may form a cathode, and a third electrode may be provided to serve as an anode. As a further alternative, each of the electrodes may form an anode, and a third electrode may be provided to serve as cathode. One electrode in the second set may form an anode and another electrode in the second set may form a cathode to sense electrical impedance across the sense electrodes and thereby sense wetness. In some examples, electrodes in the first and second sets of electrodes may be used to perform both stimulation and sensing functions.

A wetness sensor may include the second set of at least two conductive electrodes. When a conductive path is established (due to leakage of conductive fluids) between the electrodes in the second set of electrodes that straddle the urethra meatus, a circuit may trigger to generate an indication of leakage, e.g., based on an impedance change. Because of the vicinity of the clitoris/penis and the urethra, it may be desirable that the whole closed-loop system including sensing, stimulation, and control modules be able to be encapsulated in a patch- or pad-like form factor, which may be worn inside of underwear. In other words, the proximity of the stimulation site at the clitoris or penis to the leakage/wetness sensing site near the outlet of the urethra may advantageously permit the stimulation and sensing components to be located relatively close to one another and carried on or within the same carrier or housing. For example, the stimulation and sensing components may be within approximately 8-14 cm of one another. In some examples, an external stimulator configured for use by a female may have the stimulation and sensing components within approximately 10 cm of one another. In some examples, an external stimulator configured for use by a male may have the stimulation and sensing components within approximately 12 cm of one another. For example, the external stimulator may have a unitary housing, which may be applied to the patient directly or via a sheath, as described above.

In one example for male patients, the external stimulator of the closed-loop DGN stimulation system may include a ring-like member having a plurality of electrodes. The ring-like member may carry sense electrodes, sensing circuitry and stimulation generator circuitry. The ring-like member may be a continuous, closed ring, or be partially closed and include an opening in an otherwise continuous ring. In some examples, the ring-like member of the external stimulator may include at least four electrodes, including a first set of at least two electrodes positioned for placement at approximately the 10 and 2 o'clock positions on the shaft of the penis or near the base of the penis for DGN stimulation, and a second set of at least two electrodes positioned for placement close to approximately the 6 o'clock position for wetness sensing.

In another example for male patients, the external stimulator for the closed-loop DGN stimulation system may include a ring-like member having a plurality of electrodes and a patch containing at least the stimulation generator. The patch and the ring-like member may be connected by at least one lead.

The 10, 2 and 6 o'clock positions may be considered relative positions around the interior surface of the ring-like member. Upon placement of the ring-like member on the penis, the 10, 2 and 6 o'clock positions may have an arbitrary relationship with the penis, depending on the rotational angle at which the ring-like member is positioned. However, it may be desirable to rotate the ring-like member, or place the ring-like member with a particular rotation, so that the electrodes at the 10 and 2 o'clock positions straddle a portion of the penis carrying the dorsal genital nerves, such as portion on the side of the penis adjacent the DGN and corpora cavernosa and opposite the urethra. In this case, the electrodes at the 6 o'clock position may be positioned at a portion of the penis adjacent the urethra and opposite the DGN and the corpora cavernosa.

In some examples, all of the electrodes may be on an interior surface of the ring-like member. In other examples, stimulation electrodes at the 10 o'clock, 2 o'clock and 6 o'clock positions may be on an interior surface of the ring-like member, while six o'clock sense electrodes may be on either an interior or exterior surface of a tail-like section or extension of the ring-like member that extends outward from a main ring section. When placed on the penis, the main ring section may be positioned proximate the base of the penis and the tail-like extension may be positioned distal to the base of the penis. The tail-like extension may be flexible and can be made to be any desirable length to best locate urine detection. In some examples, the stimulation cathode electrodes may be placed between approximately 60 degrees and approximately 120 degrees apart, with a stimulation anode electrode approximately evenly spaced from the stimulation cathode electrodes and located at approximately the 6 o'clock position. The tail-like extension may carry the sense electrodes for placement at approximately 6 o'clock in the cross-section view of FIG. 11, e.g., adjacent the side of the penis shaft closer to the urethra. In some examples, the tail-like extension may be placed approximately 180 degrees from the midpoint between the stimulation electrodes. The approximately 6 o'clock position on the shaft of the penis for the sense electrodes may be advantageous because the tail-like extension may be captured between the penis shaft and scrotum closer to the urethra outlet. In other examples, however, the sense electrodes may be placed at different positions.

For example, as an alternative, the tail-like extension may be configured to terminate to a small, soft cup-like element, in which the glans of the penis would be placed, thereby capturing leaked urine. In some examples, the cup may be made of silicone or gauze, for example. In this example, the sense electrodes may be positioned within the cup to thereby readily detect the leaked urine. For this cup configuration, the tail-like extension may need to be flexible to accommodate different penis shaft lengths and changes in length and for comfort. For example, the tail-like extension could be in the form of coil that can contract and stretch as needed to place the cup over the glans of the penis.

In other examples, the wetness or leaked volume can be detected by sensors, such as electrodes and associated circuitry, embedded in a smart sense pad or diaper. The pad or diaper may be a separate device that is physically coupled to the external stimulator in the form of a pad-, patch- or ring-like stimulator to communicate sensor signals, e.g., via wires, from the sensor circuitry to the stimulator to activate operation of the stimulator, and form the closed-loop DGN stimulation system, together with the stimulator.

Alternatively, the sense pad or diaper may be part of an integrated device that is physically integrated with the external stimulator to form an overall stimulator system in a pad or diaper. In this example, the entire DGN stimulation system, including circuitry and other components for sensing, stimulation and control can be embedded in a sense pad or diaper form factor, and the pad or diaper may carry or be integrated with an external stimulator device housing member, such as a pad- or patch-like member for a female patient or a ring-like member for a male patient.

As a further alternative, the pad or diaper may be a separate device that is telemetrically coupled to the external stimulator in the form of a pad-, patch- or ring-like stimulator, e.g., by wireless telemetry, to communicate sensor signals from the sensor circuitry to the stimulator to activate operation of the stimulator, and form the closed-loop DGN stimulation system, together with the external stimulator.

The parameters of the stimulation may be selected to achieve a desired therapeutic effect. As an illustration, for urinary incontinence, the desired therapeutic effect may be an increase in bladder contraction frequency or strength. A stimulation program can be selected to deliver and control based on the sensing of wetness and/or sensing of a leaked volume. For example, a more intense stimulation program, e.g., where electrical stimulation and/or mechanical stimulation are more intense, may be delivered when a larger volume of leakage is detected. The volume of leakage or severity of leakage may be determined by comparing impedance levels to predetermined thresholds, for example. Hence, different stimulation intensities may be used for different volumes of detected leakage, wherein stimulation intensity may be selected as a function of leakage volume. Upon sensing wetness, without necessarily sensing a larger volume of leakage, stimulation may be activated and delivered at a relatively lower intensity than the intensity of stimulation delivered when a larger volume of leakage is detected by the sensor.

An external stimulator forming a closed-loop DGN stimulation system can provide a non-invasive incontinence therapy, e.g., for urinary or fecal voiding dysfunction. Taking advantage of the shallowness of the DGN below the skin of a patient and the proximity between the DGN nerve endings and the urethra meatus, the closed-loop system does not involve piercing the skin or an implant of a device, and may be formed as a self-contained unit in a compact form factor that is easy to wear. The external DGN stimulator may support on-demand stimulation, e.g., in response to sensed wetness, that can eliminate a patient's need to control the stimulator, as well as provide a better outcome due to the timeliness of the activation in relation to the onset of wetness. The closed-loop system can also improve therapy efficacy over time, possibly serving as a bladder training system to strengthen neural pathways that are not responding in a timely fashion under a disease state.

In some examples, the external DGN stimulator generally operates as a therapy device that delivers electrical stimulation therapy and/or mechanical stimulation therapy. The external DGN stimulator may deliver electrical stimulation therapy to a patient by generating and delivering a programmable electrical stimulation signal (e.g., in the form of electrical pulses or a continuous waveform) to target therapy sites proximate two or more electrodes. In some examples, a medical device programmer may be used to program and control the operation of the closed-loop DGN stimulation system. The programmer may include a user interface that receives input from a user. The programmer may be an external programmer that is operated by a clinician or other caregiver, e.g., in the case of a so-called clinician programmer, or by a patient in the case of a so-called patient programmer. In some examples, the patient programmer may include less programming functionality that the clinician programmer. Alternatively, the same type of programmer may be used by both the patient and the clinician or caregiver.

In some examples, the external DGN stimulator may operate to store sensed data relating to wetness and/or leakage volumes, and/or data relating to delivery of stimulation, e.g., in data storage device of the stimulator. Additionally, or alternatively, the external DGN stimulator may transmit such data to an external programmer for storage in a data storage device of the programmer. The programmer may form part of the closed-loop DGN stimulation system and may be, for example, a handheld computing device, a computer workstation, or networked computing device, or any other computing device. In other examples, the external, closed-loop DGN stimulation system may not include an external programmer, or not require such a programmer for operation, and could include a simple on/off button on the patch- or pad-like member or ring-like member.

A user such as a clinician may interact with the programmer to program the external DGN stimulator, e.g., to select values for the electrical stimulation parameters with which the stimulator generates and delivers stimulation and/or other operational parameters of the stimulator. A user such as a patient or caregiver may interact with the programmer to control the stimulator to deliver the electrical and/or mechanical stimulation therapy, to select programs for delivery of electrical and/or mechanical stimulation, to manually stop the delivery of the electrical stimulation therapy by the stimulator, or to inhibit the delivery of electrical and/or mechanical stimulation therapy by the stimulator. In some cases, a patient or caregiver may use the programmer to adjust intensity of stimulation, e.g., by adjusting amplitude, pulse rate and/or pulse width.

FIG. 1 is a block diagram illustrating example components of an external, closed-loop DGN stimulation system 10. In the example of FIG. 1, system 10 includes processor 40, stimulation generator 42, memory 44, telemetry module 46, power source 48, and sensing circuitry 50. Memory 44 may store data defining one or more therapy programs 52 for execution by processor 40 to control stimulation generator 42. In other examples, system 10 may include a fewer or greater number of components. Stimulation generator 42 is coupled to a first set of two or more electrodes 54A, 54B for delivery of electrical stimulation to the patient. Sensing circuitry 50 is coupled to a second set of two or more electrodes 56A, 56B to sense wetness and/or leakage volumes. Although two electrodes are shown in each set, more electrodes may be provided and used on a selective basis to sense wetness.

System 10 may comprise any suitable arrangement of hardware, alone or in combination with software and/or firmware, to perform the techniques attributed to system 10 and processor 40, stimulation generator 42, sensing circuitry 50 and telemetry module 46 of system 10. In various examples, processor 40 can include any one or more microprocessors, digital signal processors (DSPs), application specific integrated circuits (ASICs), field programmable gate arrays (FPGAs), or any other equivalent integrated or discrete logic circuitry, as well as any combinations of such components. Memory 44 may be any volatile or non-volatile media, such as a random access memory (RAM), read only memory (ROM), non-volatile RAM (NVRAM), electrically erasable programmable ROM (EEPROM), flash memory, or the like.

Although processor 40, stimulation generator 42, sensing circuitry 50 and telemetry module 46 are described as separate modules, in some examples, processor 40, stimulation generator 42, sensing circuitry 50 and telemetry module 46 can be functionally integrated. In some examples, processor 40, stimulation generator 42, sensing circuitry 50 and telemetry module 46 may correspond to individual hardware units, such as ASICs, DSPs, FPGAs, or other hardware units.

Memory 44 stores stimulation therapy programs 52 that specify mechanical stimulation parameter values and/or electrical stimulation parameter values for the stimulation therapy generated and delivered by system 10. In some examples, memory 44 also stores sensed data, which processor 40 may use for controlling the delivery of the stimulation therapy.

Stimulation generator 42 is configured to generate and deliver electrical stimulation to tissue of patient 12 via electrodes 54A, 54B, which are positioned on the stimulator for placement adjacent the DGN in a female or male patient when the stimulator is attached to the patient. In some examples, stimulation generator 42 may also, or alternatively, provide mechanical stimulation, e.g., in the form of vibratory stimulation, which may be generated by a piezoelectric element or other vibrating transducer. The mechanical stimulation may be delivered to a surface of the patient, and may be delivered alone or in combination with the electrical stimulation. Accordingly, while stimulation generator 42 is described herein as generating and delivering electrical stimulation, stimulation generator 42 may additionally or alternatively be configured to provide mechanical stimulation. In some examples, instead of, or in addition to, electrodes 54A, 54B, system 10 may include a plurality of actuating members that bear against the skin and transmit vibration or movement to the patient, thereby stimulating the DGN.

Processor 40 may control stimulation generator 42 by selectively accessing and loading at least one of stimulation therapy programs 52 from memory 44. Using the program, processor 40 may control stimulation generator 42. In some cases, a clinician or patient may select a particular one of therapy programs 52 from a list using a programmer, such as a patient programmer or a clinician programmer. Processor 42 may receive such a selection via telemetry module 46.

Stimulation generator 42 generates and delivers stimulation therapy, i.e., electrical stimulation and/or mechanical stimulation, according to a set of stimulation parameter values defined by the therapy program 52. In some examples, stimulation generator 42 delivers therapy in the form of electrical pulses. For pulses, relevant stimulation parameters defined by therapy program 52 include voltage or current amplitude, pulse rate, and/or pulse width. In other examples, stimulation generator 42 delivers electrical stimulation in the form of continuous waveforms. For continuous waveforms, relevant stimulation parameters defined by program 52 may include a voltage or current amplitude, a frequency, a shape of the stimulation signal, and/or a duty cycle of the stimulation signal. Also, therapy program 52 may define polarities and combinations of electrodes 54A, 54B, particularly when three of more electrodes are provided for selective use in delivering stimulation.

Closed loop therapy may allow processor 40 and stimulation generator 42 to deliver efficacious therapy to the patient 12 by timing the delivery of stimulation to respond to a specific physiological state of the patient (e.g., a particular instance of incontinence sensed by wetness or leakage volume) or an activity of the patient (e.g., social activity, sexual activity, exercise or the like). For example, closed loop therapy may enable processor 40 to control stimulation generator 42 to generate and deliver electrical stimulation to the patient 12 to help avoid or stop an episode of incontinence by the patient at an appropriate time, e.g., when the patient is at the onset of incontinence.

Telemetry module 46 includes any suitable hardware, firmware, software or any combination thereof for communicating with another device, such as a medical device programmer. Telemetry module 46 may be optional in some examples. If telemetry module 46 is provided, processor 40 controls telemetry module 46 to exchange information with a medical device programmer.

Under the control of processor 40, telemetry module 46 may receive downlink telemetry, e.g., patient input, from and send uplink telemetry, e.g., an alert, to the programmer with the aid of an antenna, which may be internal and/or external. Processor 40 may provide the data to be uplinked to the programmer and the control signals for the telemetry circuitry within telemetry module 46, and receive data from telemetry module 46. Processor 40 may transmit operational information and receive stimulation programs or stimulation parameter adjustments via telemetry module 46. Also, in some examples, system 10 may communicate with other medical devices, such as other stimulators, control devices, or sensors, via telemetry module 46.

Power source 48 delivers operating power to the components of system 10. Power source 48 may include a battery and a power generation circuit to produce operating power. In some examples, the battery may be rechargeable to allow extended operation. In other examples, power source 48 may include a non-rechargeable battery.

Figure 2:
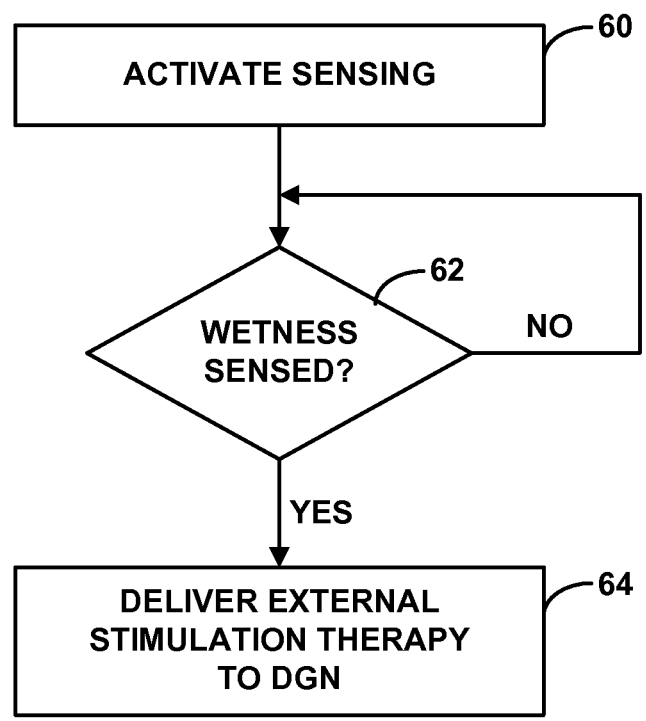
FIG. 2 is a flow diagram illustrating an example of operation of the medical device shown in FIG. 1.

FIG. 2 is a flow diagram illustrating an example closed loop technique implemented by an external DGN stimulation system, such as system 10 of FIG. 1, where system 10 includes an external DGN stimulator as described in this disclosure. In the technique shown in FIG. 2, processor 40 activates sensing by sensing circuitry 50, e.g., upon attachment of the stimulator to the patient and/or periodically after attachment. If wetness is sensed (62) or, alternatively, if a threshold volume of leakage is sensed, then processor 40 controls stimulation generator 42 to deliver external, electrical and/or mechanical stimulation to the DGN (64). The stimulation may be selected to alleviate, eliminate or reduce the severity of an incontinence episode. The intensity of the stimulation may be adjusted, in some examples, based on a volume of leakage sensed by sensing circuitry 50. For example, processor 40 may control stimulation generator 42 to deliver stimulation with a relatively greater intensity for a relatively greater sensed leakage volume, than for a relatively lower sensed leakage volume.

In some examples, as described above, processor 40 may additionally, or alternatively, control stimulation generator 42 to deliver stimulation in response to other trigger events such as patient input (e.g., a command requesting delivery of stimulation) or scheduled or timed therapy events (e.g., according to a calendar, clock or timer). Hence, in other examples, the trigger event may be a time of day, expiration of a timer, or patient input. If processor 40 does not sense wetness ("NO" branch of block 62), then processor 40 may continue sensing without activating stimulation. Upon initiation of stimulation, system 10 may stop stimulation after a predetermined period of time has elapsed. In some examples, alternatively or additionally, system 10 may be configured to automatically deliver stimulation at predetermined time intervals on an intermittent basis. As discussed above, as one example, stimulation intervals for electrical stimulation and/or mechanical stimulation may range from 3 times a day to once a week, e.g., for a duration of 5-30 minutes each time.

Figure 3:
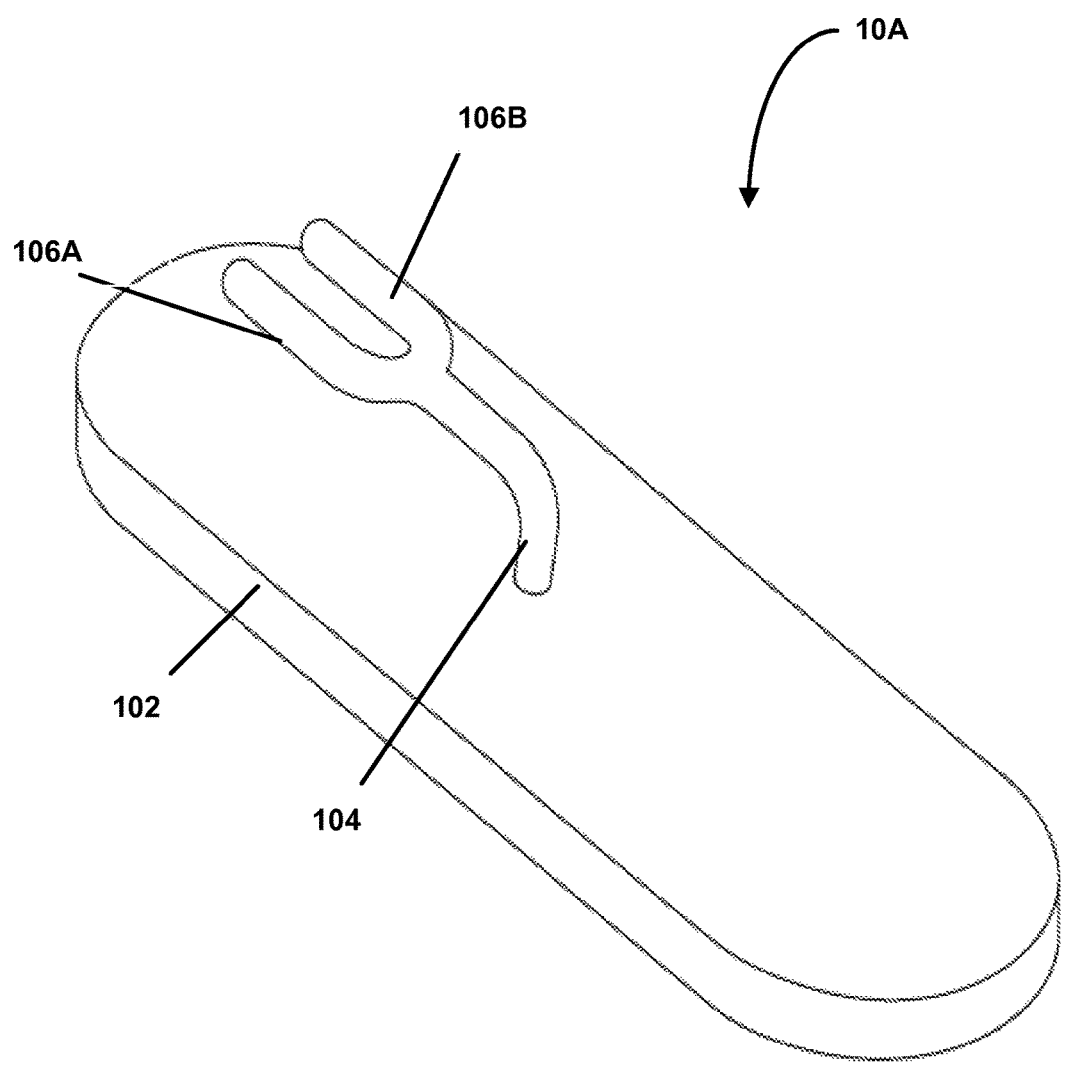
FIG. 3 is a conceptual diagram of an example of the medical device of FIG. 1, configured to deliver external DGN stimulation to a female patient.

FIG. 3 is a conceptual diagram of an example of the medical device of FIG. 1, configured to deliver external stimulation to the DGN of a female patient. The medical device of FIG. 3 forms an external DGN stimulator system 10A for a female patient as described above and with reference to FIGS. 1 and 2, and will be referred to as a stimulator 10A. In the example of FIG. 3, the medical stimulator is an external stimulator 10A that includes a patch- or pad-like device housing member 102, e.g., like a panty liner that can be placed in the underwear of a female patient for placement against a stimulation site. The stimulator 10A may be configured to be temporarily attached to the skin at the midline in the clitoris area, or slightly above the clitoris, in a female patient.

In some examples, stimulator 10A may be adhesively attached to the underwear of the female patient, or attached by other fasteners such as hook-and-look fasteners, snap-fit fasteners, press-fit fasteners or the like. Alternatively, or additionally, the stimulator 10A may be adhesively attached to the skin on the patient. The stimulator 10A may include flex circuit electronics that form stimulation and/or sensing circuitry. The flex circuit electronics may be hidden within the patch- or pad-like member 102 or placed on another side of the patch- or pad-like member 102 opposite the side to be placed against the patient's skin in the area of the clitoris.

In additional examples, the device of FIG. 3 may be configured to be enclosed or encapsulated within a bag-like or box-like sheath, or to interface with a sheet-like sheath. In these examples, the sheath may include at least one layer interposed between the stimulator and the skin of the patient, and may include electrodes for stimulation and/or sensing that interface with, or are otherwise electrically coupled to, respective stimulation and/or sensing electrodes on the stimulator.

As shown in FIG. 3, the external stimulator 10A may include a soft pliable lead 104 that carries electrodes for stimulation of the DGN. In this example, the soft pliable lead 104 carries electrodes (not shown in FIG. 3) that may be configured and positioned to contact the skin on the patient upon application of the stimulator 10A to the skin to deliver stimulation to the DGN of the clitoris. The lead 104 may extend outward from the patch- or pad-like member 102 to straddle the clitoris area or the area slightly above the clitoris adjacent the DGN. The lead 104 may be elevated from the surface of the patch- or pad-like member 102 or extend along and in contact with the surface of the patch- or pad-like member 102. The lead 103 may include bifurcated branches 106A and 106B, each of which may be placed on a respective side of skin midline of the clitoris area, and each of which may carry one or more electrodes. In this manner, the electrodes on the soft, pliable lead 104 are oriented to stimulate the DGN of the clitoris of a human patient.

The overall size of the electronics in the DGN stimulator 10A may be somewhat dependent on the battery size. If this stimulator 10A is designed to wait to sense a leak before providing stimulation, then that battery could be relatively small. If the stimulator 10A also proactively stimulates, e.g., intermittently, to try to prevent a leak in the first place (e.g., to calm overactive bladder), then a larger battery may be required.

The overall size of the DGN stimulator 10A may be approximately the same size as a normal panty-liner or pad. For example, stimulator 10A may be between approximately 8 inches and approximately 12.5 inches long, between approximately 2 inches and 3 inches wide, and between 0.125 and 0.5 inches thick. In some examples, the pad-like DGN stimulator 10A may be thicker than a normal panty-liner or pad. For example, the pad-like DGN stimulator 10A may be up to approximately 1 inch thick.

The distance between the stimulation electrodes may be selected to place the electrodes over the DGN of the clitoris. The distance between the sense electrodes may be selected to provide sufficient sensitivity for detecting leaked urine between the electrodes. The farther away from each other the sense electrodes are, the more urine may be required to bridge the gap between the sense electrodes to change impedance and trigger detection of urine leakage. Competing against proper detection is a false detection due to sweat, and this may be more likely the closer the sense electrodes are together. It may be desirable to have a hydrophilic coating (or just a fabric covering) over the electrodes to act as a collector and capture the urine and maintain an impedance change between the electrodes. Such a coating also may be used for sense electrodes in a ring-like stimulator. In general, as one example, the gap between the sense electrodes may be approximately 2 to 8 millimeters.

Figure 4:
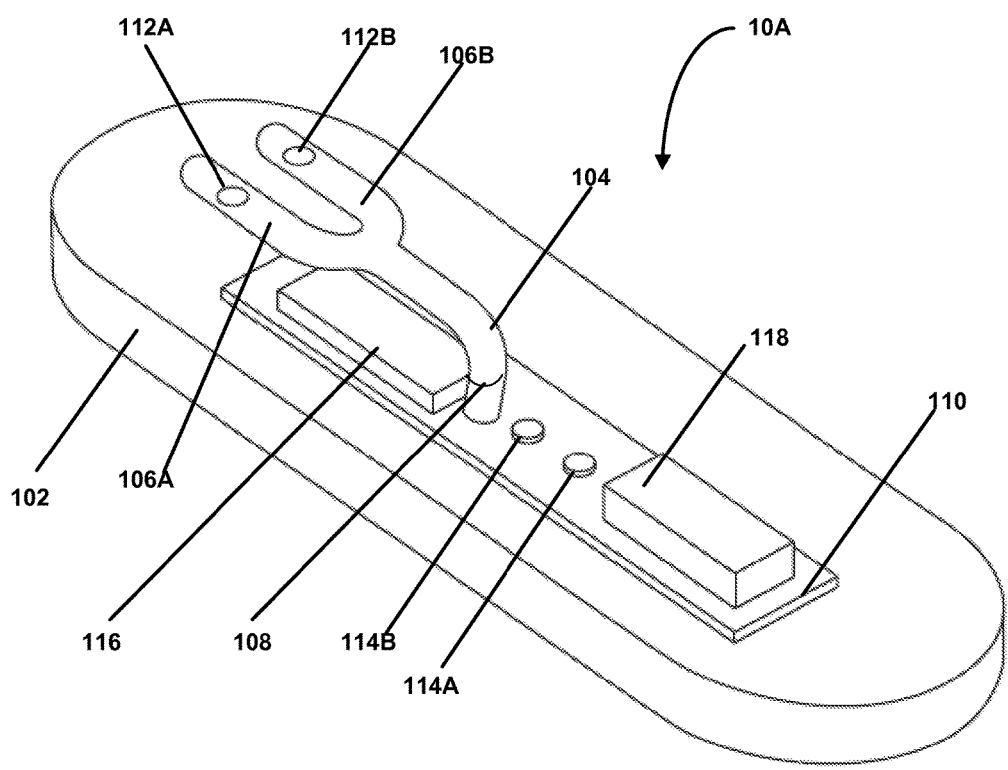
FIG. 4 is a conceptual diagram illustrating an example of various features of the medical device of FIG. 3.

FIG. 4 is a conceptual diagram illustrating an example of various features of the medical device of FIG. 3. Again, the medical device of FIG. 3 forms an external DGN stimulator system 10A for a female patient as described above and with reference to FIGS. 1 and 2, and will be referred to as a stimulator 10A. In the female patch- or pad-like example (or "panty liner" example) of the external DGN stimulator 10A, flex circuit substrate 110 and the flex circuit components 114, 116, and 118 may be embedded within or placed on a patch- or pad-like member 102. In some examples, the patch- or pad-like member 102 is a moisture absorbing pad. In the example of FIG. 4, the flex circuit electronics are shown within pad-like member 102, e.g., below a pad surface 108 from which a lead 104 protrudes. The patch- or pad-like device housing member 102 may take a variety of forms and serves as a carrier for the pliable lead 104 and the flex circuit substrate 110. In some examples, the patch- or pad-like device housing member 102 may be made from silicone, polyurethane or other medical grade materials. The materials may be soft and somewhat flexible. In this example, in FIG. 4, the flex circuit substrate 110 is shown as being embedded (e.g., by molding, extrusion or other processes) within the patch- or pad-like member 102. In other examples, shown in FIGS. 5 and 6 discussed below, the flex circuit 110 may be on a side of the patch- or pad-like device opposite lead 104. The flex circuit substrate 110 may be made of various materials including silicone, polyurethane, liquid crystal polymer, titanium, polyimide or other materials suitable for temporary or prolonged external contact with a patient.

For example, the flex circuit substrate 110 may be placed on the pad-like member 102. In some examples, the flex circuit substrate 110 can be placed on the same side of the patch- or pad-like member 102 that carries the lead 104 and faces the clitoris upon placement, on a side of the patch- or pad-like member 102 opposite the lead 104 and the clitoris upon placement, or embedded within the patch- or pad-like member 102. With further reference to FIG. 4, the soft, pliable lead 104 extends from a flex circuit substrate 110 and the pad surface 108, and includes stimulation electrodes 112A and 112B to stimulate the DGN of the clitoris. The lead 104 may include internal conductors to electrically couple the stimulation electrodes 112 to stimulation circuitry on the flex circuit substrate 110. Stimulation electrodes 112A and 112B may provide electrical stimulation. In some examples, instead of stimulation electrodes 112, stimulator 10A may include mechanical transducers and provide mechanical stimulation. In some examples stimulator 10A may include a combination of both electrical stimulation electrodes and mechanical transducers in order to provide both electrical and mechanical stimulation. In examples where both electrical and mechanical stimulation are provided, stimulation electrodes 112 may include at least two sets of electrodes. A first set of stimulation electrodes 112 may be electrodes configured to provide electrical stimulation, and a second set of mechanical transducers configured to provide mechanical stimulation.

Also, as shown in FIG. 4, the flex circuit substrate 110 carries sensing electrodes 114A and 114B that form part of the sensing circuitry and are used to detect wetness, e.g., urine leakage. The urine leakage can be sensed by an electrical impedance change observed across the sensing electrodes. The sensing electrodes 114 may be exposed by the patch- or pad-like member 102 on a side of flex circuit substrate 110 opposite the stimulation electrodes 112 or, as shown in FIG. 4, on a side of flex circuit substrate 110 adjacent the stimulation electrodes 112. For example, the sense electrodes 114 may have conductive surfaces that extend outside of the patch- or pad-like member 102. The sense electrodes 114 may be formed on the flex circuit substrate 110 and electrically coupled to sense circuitry within electronics housing 116 on the flex circuit substrate 110, or formed on a surface 108 of the patch- or pad-like member 102 and electrically coupled to sense circuitry on the flex circuit substrate 110 via electrical conductors. In some examples, sense electrodes 114 may be formed on the flex circuit substrate 110 and positioned below (away from patient 12) patch- or pad-like member 102. In such examples, patch- or pad-like member 102 may be a moisture absorbing pad. In response to sensing of wetness or detection of a volume of leakage via the sensing electrodes and sensing circuitry, the stimulation generator of the external stimulator delivers stimulation via the stimulation electrodes 112A, 112B. In some examples, a battery housing 118 may also be located on flex circuit substrate 110. The battery housing 118 may include one or more additional components, including for example, a telemetry module.

As an example, a 180 mAh rechargeable battery is approximately 0.75 inches square and 0.125 inches high. This battery size may provide a reasonable battery to provide approximately 8 hours of operation according to some stimulation protocol and leak detection. The electronic circuitry to sense leakage, generate a stimulation waveform and recharge the battery might be approximately the same volume as the battery (plus some antenna volume). In some examples, the battery housing 118 may be between a size of 0.5 inches wide×1.0 inch long×0.10 inches thick and a size of approximately 1.5 inches wide×3.0 inches long×0.3 inches thick.

The stimulation and sensing electrodes are shown as small circles in FIG. 4. The fork-like branches 106A and 106B of the lead 104, which carry the stimulation electrodes 114, may be oriented such that the distal ends of the branches 106 point upward toward the pubis of patient 12 upon placement of the stimulator 10A on patient 12. Alternatively, the branches 106 could be oriented so that the branches 106 point downward, away from the pubis. In some examples, the lead 104 and branches 106 may include some amount of spring bias to bias the electrodes 112 against the skin of the patient 12 when the stimulator 10A is placed on the patient 12, promoting reliable electrical contact. For example, the pad-like stimulator 10A may be adhesively attached to underwear and/or the skin of the patient, and the spring bias may urge the stimulation electrodes 112 against the skin of the patient to stimulate the DGN.

The flex circuit electronics of the stimulator of FIG. 4 may further include a processor, memory, stimulation generator, sensing circuitry, telemetry circuitry and power source, e.g., as shown in FIG. 1. The flex circuit electronics may be distributed between housing 116 and housing 118. The power source may be a battery. These components may be carried by the patch- or pad-like member 102 on the flex circuit substrate 110. Alternatively, some or all of these components, including the electronics, battery and lead may be positioned to attach to the skin above the clitoris on the pubis of the female patient.

In some examples, in addition, or as an alternative, to electrical stimulation, the patch or pad-like stimulator 10A may include a mechanical stimulator such as a piezoelectric element or other transducer to convey mechanical, e.g., vibratory, stimulation to the patient. Electrical and mechanical stimulation may be applied independently, in a selective manner, or together in a simultaneous or coordinated manner.

Figure 5:
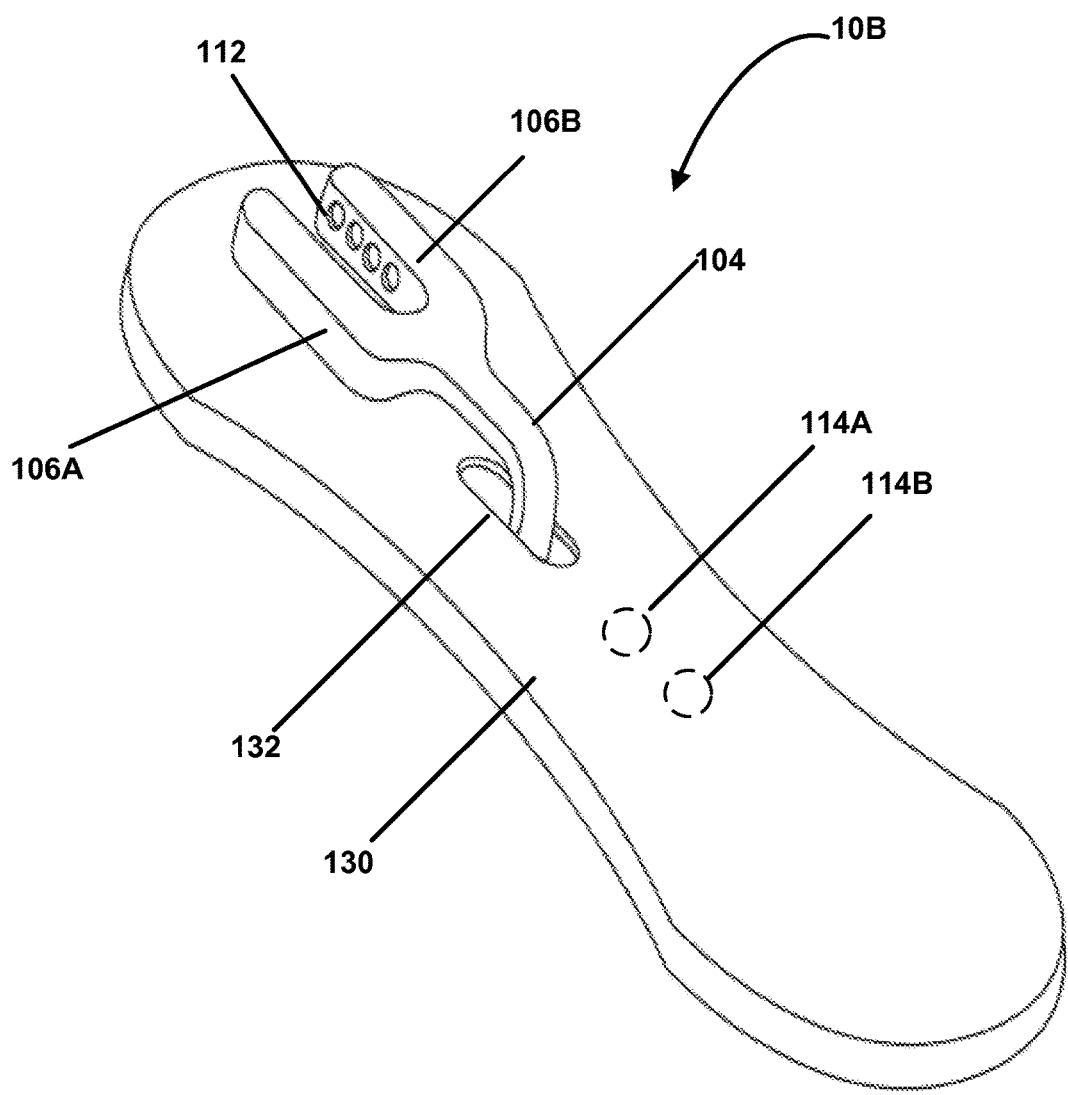
FIG. 5 is a conceptual diagram illustrating an example of the medical device of FIG. 1, configured to deliver external DGN stimulation to a female patient.
Figure 6:
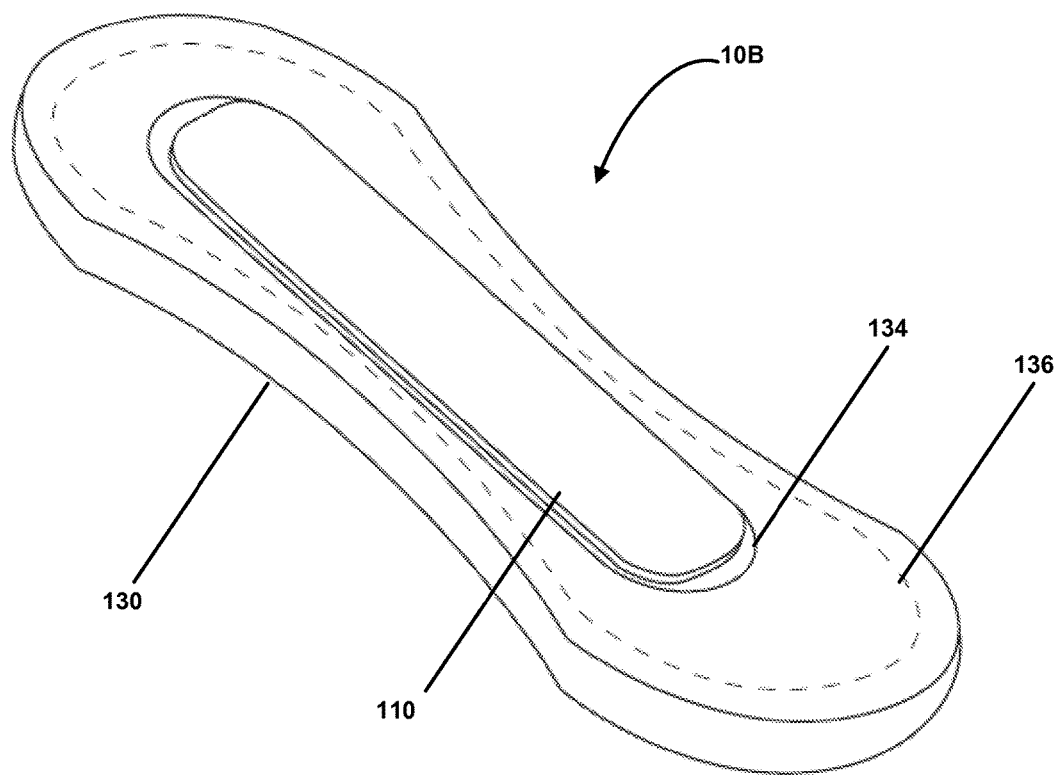
FIG. 6 is a conceptual diagram illustrating another view of the example medical device of FIG. 5.
Figure 7:
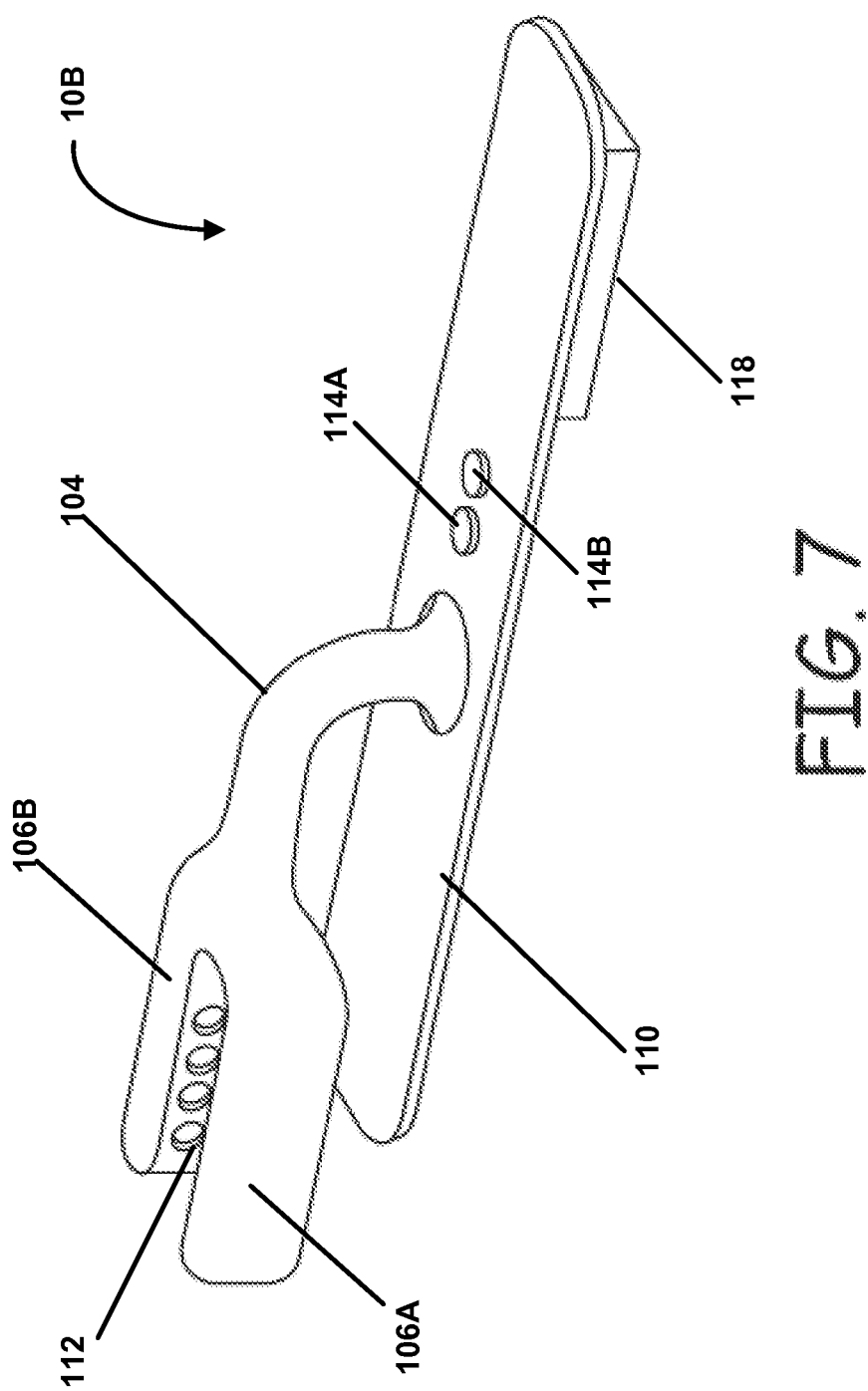
FIG. 7 is a conceptual diagram of the medical device of FIG. 5, without a pad-like member.
Figure 8:
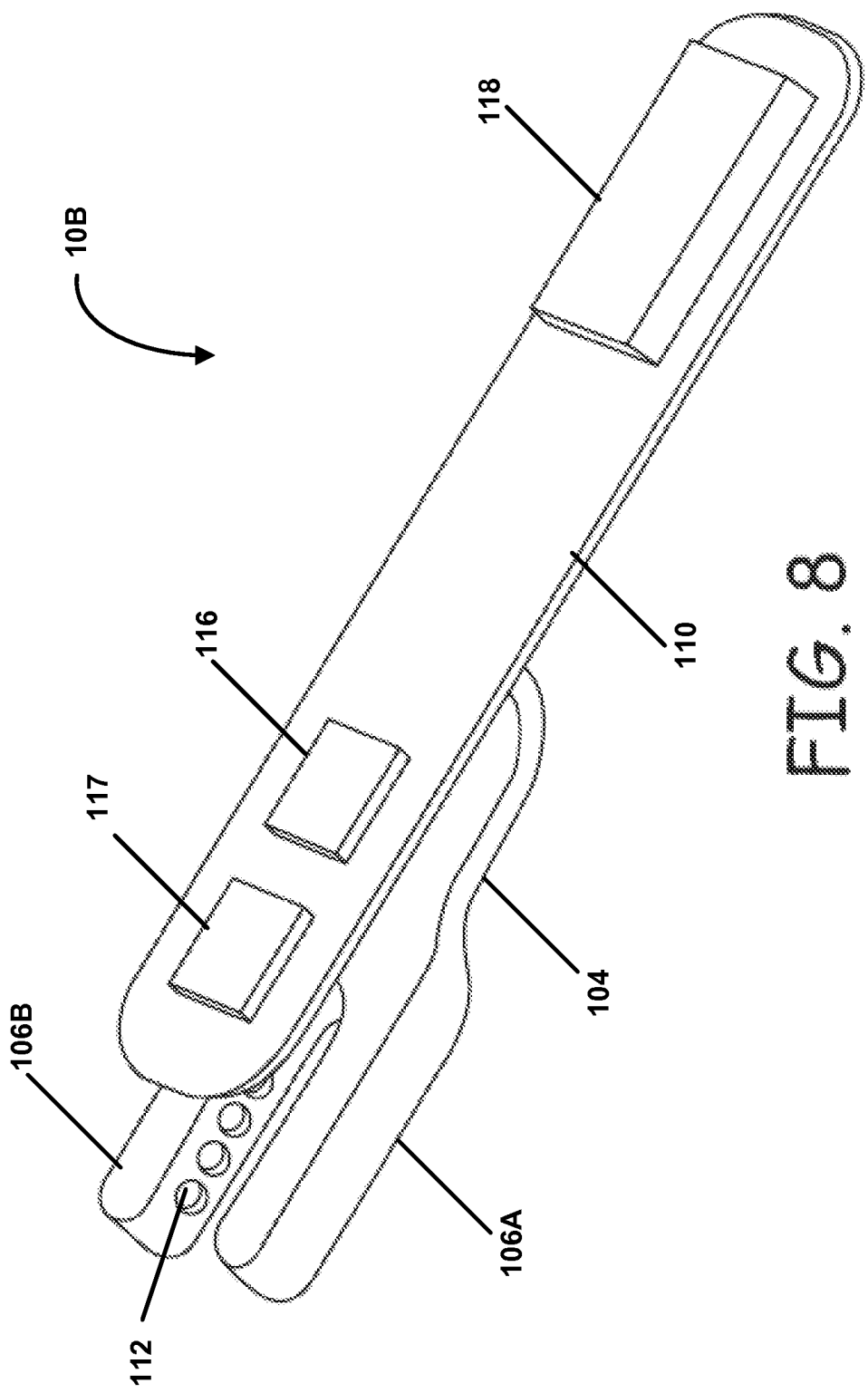
FIG. 8 is a conceptual diagram of another view of the medical device of FIG. 5.

FIG. 5 is a conceptual diagram of another example of the medical device of FIG. 1, configured to deliver external stimulation to a female patient. The medical device of FIG. 1 forms an external DGN stimulator system for a female patient as described above and with reference to FIG. 1, and will be referred to as stimulator 10B. In the example shown in FIG. 5, the medical device is an external stimulator 10B that is used in connection with a sheath 130. Sheath 130 includes an opening 132 through which lead 104 extends. Lead 104 may be configured to provide a space between flex circuitry (not shown) of DGN stimulator 10B and branches 106 for sheath 130. In addition, or alternatively, the dimensions of sheath 130 may be configured to fit between lead 104 and the flex circuit substrate. Other views of stimulator 10B are shown in FIGS. 6-8. Sensing electrodes 114A, 114B are located on the flex circuit substrate under sheath 130.

Sheath 130 may be disposable. In some examples, sheath 130 may be a moisture-absorbing pad. Lead 104 includes branches 106A and 106B. Branches 106A and 106B may be configured to position electrodes 112 on both sides of the midline of the clitoris. The electrodes 112 may be placed on branches 106 in an orientation to facilitate stimulation of the first and second DGN. Stimulator 10B includes at least two electrodes. In the example shown in FIG. 5, stimulator 10B includes four electrodes on each branch 106. During the delivery of stimulation two of the electrodes may be configured as cathodes while a third electrode is configured as a anode. The electrodes 112 may be oriented along the portion of branches 106A, 106B facing each other. In such examples, the spacing between branches 106A, 106B can be configured to allow the skin around the clitoris to be received between the branches 106A, 106B. In some examples, the lead 104 and branches 106 may include some amount of spring bias to bias the electrodes 112 against the skin of the patient 12 when the stimulator 10B is placed on the patient, promoting reliable electrical contact. The spring bias may be towards the skin of the patient and/or the branches may be biased towards one another. For example, stimulator 10B and sheath 130 may be adhesively attached to underwear and/or the skin of the patient, and the elastic force of the underwear and the spring bias of branches 106 may urge the stimulation electrodes 112 against the skin of the patient to stimulate the DGN. Stimulation may be provided by one or more electrode combinations. The electrode combination may be selected by a user based on which combination provides the most efficacious stimulation.

FIG. 6 is a conceptual diagram of another view of stimulator 10B shown in FIG. 5. FIG. 6 shows the other side of sheath 130, opposite the side shown in FIG. 5, and a flex circuit substrate 110 of stimulator 10B. As shown in FIG. 6, sheath 130 may include an indent 134 configured to house flex circuit substrate 110. Sheath 130 may be slipped over stimulator 10B and positioned so that lead 104 (not shown in FIG. 6) extends through opening 132 (also not shown in FIG. 6) while flex circuit substrate 110 rests within indent 134. In some examples sheath 130 may also include an adhesive 136 on the surface of sheath 130 shown in FIG. 6. In some examples, adhesive 136 may be used by a patient to temporarily adhere sheath 130 and stimulator 10B to underwear. When placing sheath 130 and stimulator 10B within a pair of underwear, a patient may position the sheath 130 and stimulator 10B in a manner so that stimulation electrodes 112 (not shown) are on each of the sides of the clitoris.

FIG. 7 is a conceptual diagram of the DGN external stimulator 10B of FIG. 5 without sheath 130. Flex circuit substrate 110 carries sensing electrodes 114A and 114B that form part of the sensing circuitry and are used to detect wetness, e.g., urine leakage. The urine leakage can be sensed by an electrical impedance change observed across the sensing electrodes 114, and may be sensed as leakage, e.g., based on a change in impedance, or as a volume of leakage, e.g., based on an impedance value. As shown in FIG. 7, in some examples, electronics housing 118 may be on surface of flex circuit substrate 110 opposite sensing electrodes 114. The space between branches 106 and flex circuit substrate 110 may be configured to allow a sheath 130 to be positioned in between as show in FIG. 5, for example. In some examples, the flex circuit electronics of the stimulator of FIG. 7 may further include a processor, memory, stimulation generator, sensing circuitry, telemetry circuitry and power source, e.g., as shown in FIG. 1. The flex circuit electronics may be distributed between housing 118 and another housing (not shown). That is, some electronics components may be in housing 118 while other components may be in another housing. Alternatively, all electronic components may be in a single housing. In general, a housing may be a integrated circuit chip package or other electronic package. Housing 118 may house a battery. The power source may be a battery. These components may be carried by the patch- or pad-like member 102 on the flex circuit substrate 110. Alternatively, some or all of these components, including the electronics, battery and lead may be positioned to attach to the skin above the clitoris on the pubis of the female patient.

FIG. 8 is a conceptual diagram of another view of DGN stimulator 10B. As shown in FIG. 8, the surface of flex circuit substrate 110 opposite the surface from which lead 104 extends may carry multiple housing units 116, 117, and 118. In some examples, housing 118 encloses a battery. Housing units 116 and 117 may include telemetry modules, sense and therapy stimulation processors, and a memory. The surface of flex circuit 110 and housing units 116, 117, and 118 may be coated in a soft conformal coat or silicone molding or otherwise encapsulated.

In some examples, flex circuit substrate 110 may include conductive traces (not shown) to interconnect circuit components in various housings 116, 117, and 118. The conductive traces may also connect one or more of the circuit components to either the stimulation electrodes or the sensing electrodes. Further in systems including telemetry capability, a coil antenna may be included in one of the housings on flex circuit substrate 110. In other examples, the coil antenna may be impeded in the flex circuit substrate.

Figure 9:
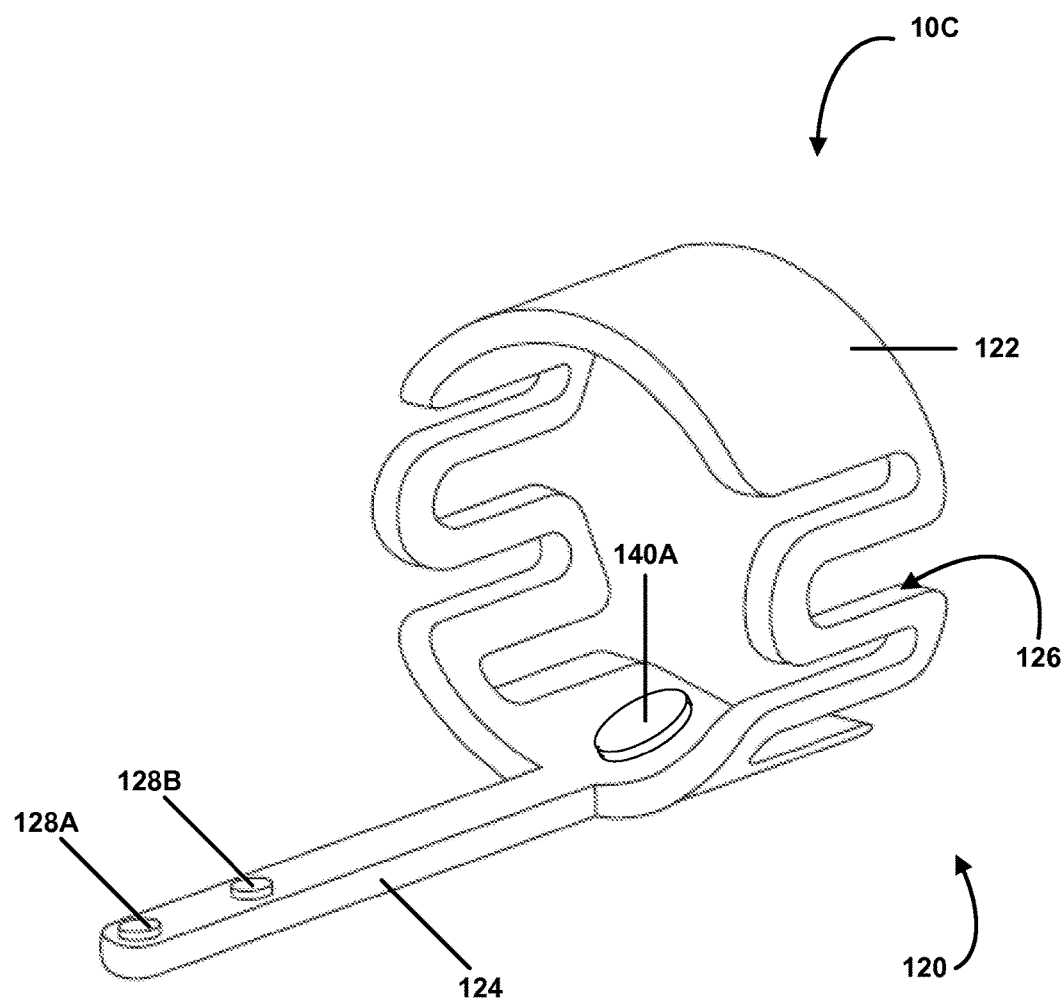
FIG. 9 is a conceptual diagram of another example of the medical device of FIG. 1, configured to deliver external DGN stimulation to a male patient.

FIG. 9 is a conceptual diagram of an example of the medical device of FIG. 1, configured to deliver external stimulation to a male patient. The medical device of FIG. 1 forms an external DGN stimulator 10C for a male patient as described above and with reference to FIG. 1, and will be referred to as stimulator 10C. In the example of FIG. 9, the medical device is an external stimulator 10C in a ring-like configuration. As shown in FIG. 9, the ring-like member 120 is sized and configured to encircle the penis shaft of a male patient. The ring-like member 120 includes a main ring section 122 and a tail section 124, one or both of which may be flexible. In some examples both the main ring section 122 and the tail section 124 may be flexible.

The main ring section 122 may be substantially continuous along its axial length or, as shown in FIG. 9, may have a wave or bend pattern 126 in at least a portion of the main ring section 122. The wave or bend pattern 126 may promote flexibility and/or patient comfort. In addition, the ring-like member120 may be formed from a flexible material. The main ring section 122 also may be continuous about its circumference, forming a closed ring. As an alternative, in some examples, the main ring section 122 may be discontinuous and include an opening in an otherwise continuous ring. The opening (not shown in FIG. 9) may be relatively small. The opening may help to promote flexibility of the main ring-like section 122, e.g., to aid in attaching the ring-like member 120 to the shaft of the penis.

The ring-like member 120 may be sized to accommodate a range of adult penis diameters. As one example, the ring-like member 120 may accommodate penis diameters in a range of approximately 11 cm circumference (=3.5 cm diameter) to approximately 8 cm circumference (=2.5 cm diameter). Ideally, one device would accommodate all diameters, but there is also the option to provide devices in different sizes. In some examples, the ring-like member 120 may have some stretch or elasticity to permit use with different penis diameters. The pitch (i.e., distance) between the stimulation electrodes 140B and 140C shown in FIG. 10) configured to be located proximate the branches of the DGN may change based on diameter of the device because it may be desirable to have the electrodes be in the same angle location on the cross section. Just as an example and using 45 degrees off from vertical, then the distance between the stimulation electrodes may be approximately ¼ (0.25) of the circumference. So, using the 11 cm and 8 cm circumference, the distance along the inner circumference of the ring-like member 120 between the electrodes may be between approximately 2.75 and approximately 2 cm. Stimulation electrode 140A is configured as an anode, and located approximately 180 degrees from the midpoint between stimulation electrodes 140B and 140C, which are configured as cathodes.

The tail section 124 supports sense electrodes 128A and 128B. The sense electrodes are configured to detect wetness. One of the sense electrodes is configured as an anode and the other sense electrode is configured as a cathode. Sensing circuitry (not shown) senses the electrical impedance between the two sense electrodes 128A and 128B. Stimulator 10C may sense wetness based on the level of the sensed electrical impedance.

Figure 10:
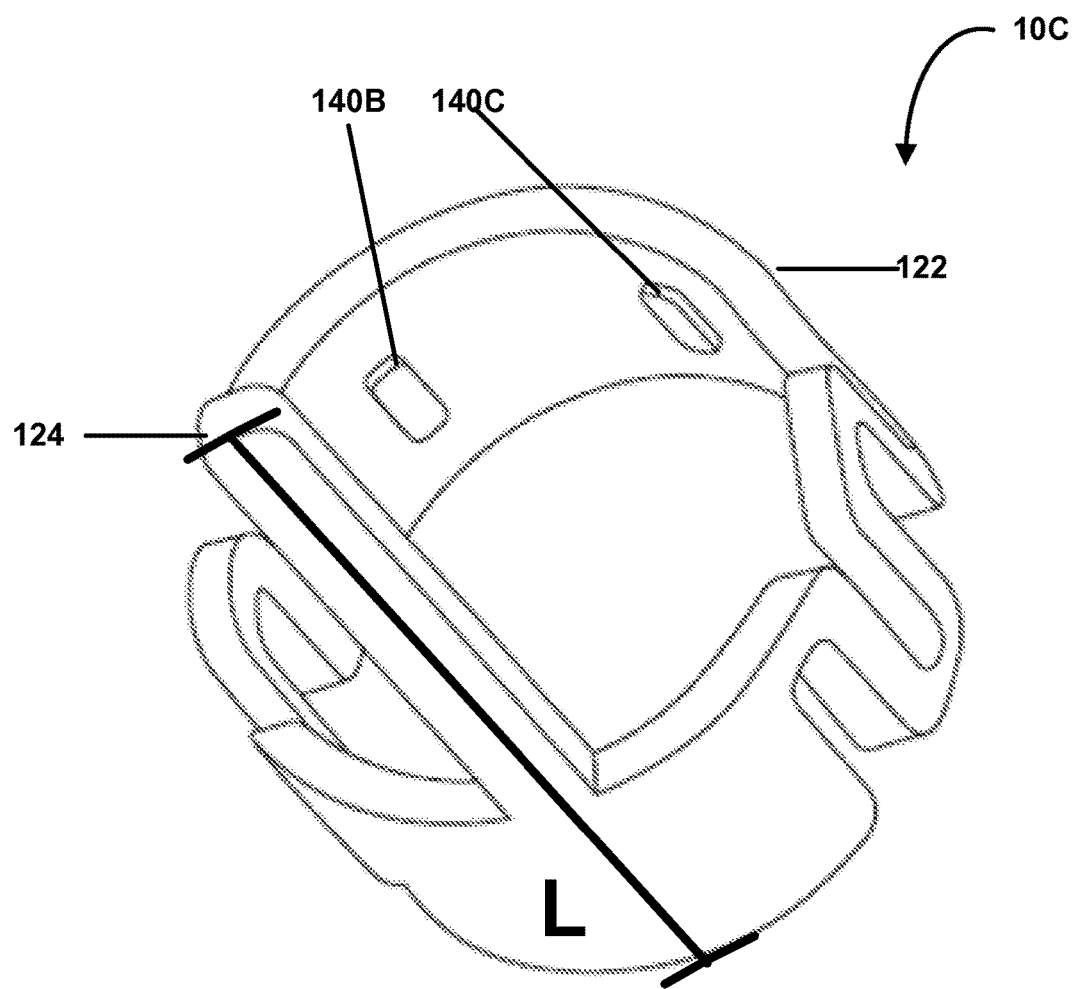
FIG. 10 is a conceptual diagram illustrating a second view of the medical device of FIG. 9.

FIG. 10 is a conceptual diagram illustrating a second view of the medical device of FIG. 9. In particular, FIG. 10 illustrates an interior surface of the main ring section 122. Again, the medical device of FIG. 10 forms an external DGN stimulator 10C for a male patient as described above and with reference to FIGS. 1 and 2, and will be referred to as stimulator 10C. As shown in FIG. 9 and FIG. 10, the main ring section 122 may include an upper section, wave-like side sections, and a lower section. Stimulation electrodes 140B and 140C may be provided on an interior surface of the upper section of the main ring section 122. The stimulation electrodes 140 may be placed at approximately 10 and 2 o'clock on the interior surface of the main ring section to straddle the DGN when the ring is placed over the penis on a side of the penis where the DGN is relatively closer to the skin surface. The sensing electrodes (not shown in FIG. 10) may be placed adjacent one another on the tail section 124 of the ring-like member 120. The total length of the tail section and the ring-like member, L, may be approximately between approximately 8 and 14 cm. In some examples, L may be approximately 12 cm. Tail section 124 may be flexible enough that any excess length may bunch within the user's underwear, thereby still positioning sense electrodes 128 in close proximity to the meatus, and allowing for detection of urine leakage.

The sensing electrodes are shown as small circles in FIG. 9. The stimulation electrodes 140 are shown as small rounded rectangles in FIG. 10. The sensing electrodes 128 on the tail section 124 are placed adjacent one another on an interior surface of the tail section 124 at approximately 6 o'clock relative to the stimulation electrodes 140 and are oriented to face inward toward the penis shaft on a side of the penis shaft opposite the side on which the stimulation electrodes 140A, 140B face, upon placement of the ring member 120 about the penis. For example, the electrodes at the 10 and 2 o'clock positions may be placed to straddle a portion of the penis carrying the dorsal genital nerve, such as portion on the side of the penis adjacent the corpora cavernosa and dorsal vein, and opposite side of the penis on which the urethra is located. In this case, the electrodes at the 6 o'clock position may be positioned at a portion of the penis adjacent the urethra and opposite the DGN, dorsal vein and the corpora cavernosa.

The ring-like stimulator 10C may be placed or rotated by the patient or a caregiver so that the stimulation electrodes 140 are placed on a side of the penis shaft adjacent the DGN and the sensing electrodes are placed on a side of the penis shaft opposite the stimulation electrodes. For example, the stimulation electrodes 126 of the ring-like member 120 may be positioned to stimulate the dorsal surface of the penis shaft where the DGN is located. In some examples, the stimulation electrodes may be positioned to straddle across the DGN, such that the stimulation electrodes are on opposite sides of the DGN, and are positioned over or adjacent to respective DGN branches at roughly 10 and 2 o'clock.

The stimulation electrodes 140 are electrically coupled to a stimulation generator, which may be formed by flex circuit electronics provided within or on the ring-like member. The sensing electrodes are electrically coupled to sensing circuitry, e.g., as described with reference to FIG. 1, which may be formed by flex circuit electronics provided within or on the ring-like member. The flex-circuit electronics may be within the main ring section, the tail section or both. Urine leakage can be sensed by an electrical impedance change observed across the sensing electrodes. In response to sensing of wetness or detection of a volume of leakage, the stimulation generator of the ring-like stimulator delivers stimulation via the stimulation electrodes to stimulate the DGN.

In some examples, the ring-like member 120 may be made from silicone, polyurethane or other medical grade materials. The materials may be soft and somewhat flexible. The flex circuit electronics may be embedded (e.g., by molding, extrusion or other processes) within or carried on the ring-like member. In some examples, a thin flexible circuit may be formed in the shape of the ring-like member, or a portion of the ring-like member. The thin flexible circuit around the penis may be connected, e.g., with thin conductive wires, to additional electronics and a battery, which may be adhered at a position adjacent to the patient's skin. The additional electronics may be connected to a patch. Alternatively, the electronics and a small recharge battery may reside on the flex circuit. Electronics such as processor, memory, stimulation generator, sensing circuitry, telemetry circuitry and power source, e.g., as shown in FIG. 1, may be distributed between the ring-like member 120 and the patch.

In some examples, in addition, or as an alternative, to electrical stimulation, the ring-like stimulator may include a mechanical stimulator such as a piezoelectric element or other mechanical transducer to convey mechanical, e.g., vibratory, stimulation to the patient. Electrical and mechanical stimulation may be applied independently, in a selective manner, or together in a simultaneous or coordinated manner.

In various examples, including the examples of FIGS. 3-10, the wetness or leaked volume can be detected by sensors, such as electrodes and associated circuitry, configured to sense changes in electrical impedance (e.g., electrical resistance) as an indication of wetness. The sensors and/or circuitry may be embedded in, or used in conjunction with, a patch- or pad-like member, as shown in FIGS. 3-8, or in a ring-like member, as shown in FIGS. 9 and 10. The sensing circuitry senses an impedance change in an area between the sense electrodes as urine leaks from the patient's urethra. For example, a decrease in impedance between the sense electrodes may indicate that a fluid is present, as the fluid more easily conducts electrical current between the two electrodes, resulting in a reduced impedance.

In some examples, different levels of sensed impedance may indicate different volumes of leakage. For example, a first level of sensed impedance less than a baseline (dry) impedance may indicate a first volume of leakage, a second level of sensed impedance less than the first level may indicate a second volume of leakage that is greater than the first volume of leakage, a third level of sensed impedance less than the second level may indicate a third volume of leakage that is greater than the second level, and so forth. Different levels of sensed impedance may be used to establish different thresholds for delivery of stimulation.

As an example, sensing impedance that is less than or equal to the first level of impedance but greater than the second level of impedance may trigger delivery of stimulation at a first intensity level, and sensing impedance that is less than or equal to the second level of impedance but greater than the third level of impedance may trigger delivery of stimulation at a second intensity level that is higher than the first intensity level. Similarly, sensing impedance that is less than or equal to a third level of impedance may trigger delivery of stimulation at a third intensity level that is higher than the first and second intensity levels. The intensity of the stimulation may be adjusted by a processor by adjusting amplitude, pulse rate, pulse width, and or duration.

Upon sensing an impedance level that is less than or equal to one of the threshold levels, the stimulator 10 may deliver stimulation for a predetermined period of time and then stop delivery of stimulation for another predetermined period of time. Upon sensing the impedance again, the stimulator may again deliver stimulation for a predetermined period of time if the impedance level is still less than or equal to a first threshold level. Alternatively, the stimulator may be configured to deliver stimulation only if the impedance level has further decreased, indicating additional leakage, to be less than or equal to a second threshold level less than the first threshold level. In this manner, the stimulator may deliver stimulation if additional leakage is detected, such that involuntary voiding has persisted. Again, intensity may be increased for different levels of impedance, corresponding to different leakage volumes. Alternatively, the stimulation may be delivered with the same intensity level when an impedance at less than or equal to a threshold impedance level is sensed.

The impedance may be sensed using any of the sense electrodes described above with reference to FIGS. 3-10. The sense electrodes may be in contact with the skin surface of the patient, and sense impedance on the skin surface between the sense electrodes. The impedance may change when urine is present on the skin surface. Alternatively, or additionally, absorbent media such as cotton or other fabrics may be placed between the electrodes to absorb leaked urine. In this case, the sense electrodes may sense the impedance between the electrodes across the skin surface and/or the absorbent media, which carries some of the leaked urine. The impedance may change as the absorbent media absorbs additional urine. The absorbent media may be disposable or washable and reusable, and may be attached to the external stimulator, e.g., with adhesive or other fasteners such as hook-and-look fasteners, snap-fit fasteners, press-fit fasteners, or the like.

Hence, in various examples, the external stimulator may sense wetness caused by urine leakage based on impedance sensed between sense electrodes placed on the skin of the patient. Different volumes of leakage may be sensed by the external stimulator based on different levels of sensed impedance. The impedance may be sensed across the skin of the patient, between the electrodes, or across the skin and/or absorbent media that absorbs leaked urine. These examples of provided for illustration. However, many other sensing devices with a variety of different configurations may be used to sense wetness and/or leakage volume to trigger external DGN stimulation in a stimulator as described in this disclosure, such as the patch- or pad-like stimulator of FIGS. 3-8 or the ring-like stimulator of FIGS. 9 and 10.

Other examples of wetness and/or leakage volume sensing systems that may be used with the external DGN stimulators described in this disclosure are described in commonly assigned U.S. Pat. No. 7,855,653, entitled External Voiding Sensor System, to Rondoni et al. (the '653 patent), the entire content of which is incorporated herein by reference. In some examples described in the '653 patent, an impedance sensor senses wetness and/or leakage volume using an array of electrodes provided in an absorbent pad. For example, impedances may be sensed across individual sets of electrodes in the array in the absorbent pad. The number of individual electrode sets that produce an impedance indicative of wetness may indicate a leakage volume. In addition to impedance sensors, the '653 patent describes other types of sensors that may be provided to sense wetness and/or leakage volume. The external DGN stimulators described in this disclosure may be configured to include the impedance sensors or other sensors described in the '653 patent to sense wetness and/or leakage volume.

The external DGN stimulators described in this disclosure may be configured to include other types of sensors and sensing systems. For example, an external DGN stimulator may be used with a system that detects urine leakage and characterizes volume of urine leaked, pad weight, or severity of the leakage by patients suffering from urinary incontinence, as described in the section below.

In one example, a flexible, disposable sense pad may be placed inside the underwear and is ideally centered over the terminus of the urethra (the urethral meatus in women or the tip of the penis in men). The sense pad has substantially fixed dimensions, although it may be flexed to fit the contour of the relevant anatomy. The sense pad has conductive contacts on opposite sides of the pad (the cross-hatched regions) and is filled with a weakly conductive, ground material such as a silicon or silicon mixed with graphene.

An example sense pad may have a curvilinear form factor. As one example, representative dimensions of the pad may be length L=10 cm, width W=6 cm and thickness T=0.5 cm. In this example, the pad may be electrically or wirelessly coupled to provide sensed impedance measurements to electronic circuitry of a patch- or pad-like or ring-like external DGN stimulator, as described in this disclosure.

Alternatively, a sensor configured in a manner similar to the sense pad may be reduced in size and placed on or form part of the patch- or pad-like stimulator or ring-like stimulator described in this disclosure. For example, the sense pad could be integrated with or form a layer of a patch-like or pad-like stimulator to sense wetness. The sense pad provided with the patch-like or pad-like stimulator could be placed in contact with the skin of the patient instead of sense electrodes, and formed to permit the stimulation electrodes to contact the skin of the patient. In a ring-like stimulator, the sense pad could be reduced in size and shaped to be placed on tail-like section or main ring section to sense wetness. The sense pad may be disposable and attached to the stimulator with adhesive or other fasteners.

When excited with either a voltage or current from one conductive contact to the other, the resulting induced current or voltage may be used to infer the bulk resistance of the pad. The resistance of the pad is given by:

$$B = \rho L / (W \times T)$$

where $\rho$ is the resistivity of the material inside the pad in ohms-meter. If pure silicon is used as the filler, the resistivity is $6.40 \times 10^2$ ohms-meter.

In the example described above with length L=10 cm, width W=6 cm and thickness T=0.5 cm, for purposes of illustration, the impedance from one electrical contact to the other electrical contact would be R=$6.40 \times 10^2$ ohms-meter* (0.1 m/(0.06 m*0.005 m))=213 kOhm. The mass (given a density of 2.33 g-cm$^3$) is 70 g. Given the disposable nature of the pad, the material is preferentially selected to minimize or reduce cost.

The filler may also be comprised of blends of different substances to modify the electrical properties of the fill. If a blended mixture of 80% silicon and 20% graphene is used, the resistivity is ($0.80*6.40 \times 10^2$ ohms-meter)+($0.20*1 \times 10^{-8}$ ohms-meter)=512 ohms-meter.

Urine is substantially more conductive than silicon. If one assumes that the resistivity of urine approximates that of sea water (roughly $2 \times 10^{-1}$ ohms-meter), the addition of urine to the pad substantially changes the impedance as measured from one conductive contact to the other. By means of example, assume it was characterized that the addition of 3 mL of urine to the pad wets 30% of the pad and the urine is evenly distributed in the pad. The impedance R would therefore be:

$$R = ((0.70*6.40 \times 10^2 \text{ ohms-meter}) + (0.30*2 \times 10^{-1} \text{ ohms-meter}))*(0.1 \text{ m}/(0.06 \text{ m}*0.005 \text{ m})) = 149 \text{ kOhm}$$

If the addition of 5 mL of urine wets 50% of the pad, the impedance would be:

$$R = ((0.50*6.40 \times 10^2 \text{ ohms-meter}) + (0.50*2 \times 10^{-1} \text{ ohms-meter}))*(0.1 \text{ m}/(0.06 \text{ m}*0.005 \text{ m})) = 107 \text{ kOhm}$$

Similarly, pad weight can be inferred from the impedance change during urine leak.

A learning algorithm may be deployed to adapt to a patient leakage pattern for better accuracy. In one example, a learning algorithm may be deployed to calibrate the estimated leaked volume based on actual measurement of the pad weight and/or leaked volume.

The leaked urine volume measurement system includes the disposable, conductive pad and a reusable electronics module, which may form part of an external DGN stimulator as described in this disclosure, that measures the impedance from one conductive contact to the other. The sensed change in impedance may be used to infer the amount of urine present in the pad.

In other example, conductive threads, which may be only slightly conductive, are woven into fabrics so as to make the fabrics conductive. These fabrics can then be used to effectively make electrical circuits that can be monitored by additional electronics to sense wetness and/or leakage volume. A representative panel of fabric could be used to make a sense pad, diaper, mattress pad, panty liner, or the like. A middle layer material may be non-conductive, while top and bottom layer fabrics are conducting. The slightly conductive materials may be woven into the middle layer. Presence of urine in the middle layer carrying the conductive threads may reduce impedance between the top and bottom layers.

The composite fabric assembly may be manufactured in large sheets. This allows the manufacturer of the pad (panty liner, etc.) to handle and process the material the same as they might with other currently marketed absorbent materials. Separate, re-useable electronics may attach to the pad and be configured to monitor the conductive fabrics. For example, the pad may be electrically or wirelessly coupled to provide sensed impedance measurements to electronic circuitry of a patch- or pad-like or ring-like external DGN stimulator, as described in this disclosure.

Urine absorbed by the non-conductive material will close the circuit between the conductive fabrics. Many-layers of conducting fabrics might detect differences in volume of leaks. End-to-end monitoring of individual conductive strip panels can be monitored for impedance changes that correlate to volume of leaks. The electronics can monitor each conductive layer from front to back and also between the conductive layers. The electronics can broadcast when a leak is detected with a calculated volume. The electronics can also store leakage metrics if desired (time stamp, frequency/day or week, volume, etc.)

In yet another example, multiple conductive strips may be inserted in a pad with various distances from the center of the pad. Depending on which circuit(s) between the conductive strips are closed, the spread of the urine in the diaper is detected and the leaked volume, pad weight, and leakage severity can be estimated.

FIG. 11 is a conceptual, cross-sectional view of a human penis, illustrating the DGN relative to other anatomical structure. As shown in FIG. 11 the human penis includes a dorsal vein 210 at approximately the 12 o'clock position. The urethra 202 is at approximately the 6 o'clock position. On either side of the dorsal vein 210 are dorsal arteries 208A and 208B. On either side of the dorsal arteries 208 are dorsal genital nerves 206A and 206B. The dorsal genital nerves 206 tend to be close to the skin surface on the dorsal side of the penis adjacent the corpora cavernosa 204. DGN 206 is a terminal branch of the pudendal nerve. In females the DGN is also referred to as the dorsal clitoral nerve. In males, the DGN is also referred to as the dorsal penile nerve. Stimulation of the DGN may cause the pelvic floor to contract, thereby preventing urine or fecal leakage associated with incontinence.

In some examples external DGN stimulation system 10 may be used alone or in conjunction with the technique of FIG. 2 in order to improve a patient's bladder control. Processor 40 controls stimulation generator 42 to deliver external, electrical and/or mechanical stimulation to the DGN. The stimulation may be selected to alleviate, eliminate or reduce the severity of an incontinence episode. In some examples the stimulation may be selected to provide an indication or reminder to a patient, e.g., a sensation that reminds the patient to control pelvic floor muscles to avoid or stop an incontinent event such as urine leakage. The stimulation may be delivered in a closed-looped fashion as described with respect to FIG. 2, i.e., in response to sensing of leakage. In some examples, as described above, processor 40 may additionally, or alternatively, control stimulation generator 42 to deliver stimulation in response to other trigger events such as patient input (e.g., a command requesting delivery of stimulation) or scheduled or timed therapy events (e.g., according to a calendar, clock or timer).

In response to the delivery of external stimulation therapy, the patient may be reminded to contract their pelvic floor muscles. The manual contraction of the pelvic floor muscles may aid in the alleviation of the current incontinence episode. In addition, by manually contracting the pelvic floor muscles in response to the stimulation, the patient's brain may be slowly trained to better regulate the patient's bladder. Over time, with repeated stimulation, the incidence of incontinence episodes may decrease, thereby reducing or eliminating the need for the external stimulation system 10. In some examples, the system 10 may be programmed to slowly increase, or eliminate the application of scheduled or time therapy events.

The techniques described in this disclosure, including those attributed to system 10 programmers, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be stored on, as one or more instructions or code, a computer-readable storage medium and executed by a hardware-based processing unit. Computer-readable storage media may include computer-readable storage media forming a tangible, non-transitory medium. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including a stimulator, an external programmer, a combination of a stimulator and external programmer, an integrated circuit (IC) or a set of ICs, and/or discrete electrical circuitry, residing in a stimulator and/or external programmer.

Various examples have been described. These and other examples are within the scope of the following claims.

What is claimed is:

1. An external stimulating device comprising:
   a stimulation generator configured to generate stimulation for stimulation of a first dorsal genital nerve and a second dorsal genital nerve of a patient;
   at least two stimulation electrodes positioned to deliver the stimulation to the first dorsal genital nerve and the second dorsal genital nerve;
   a moisture absorbing pad configured to at least partially encapsulate the stimulation generator; and
   a lead with two branches, each branch carrying at least one of the stimulation electrodes, wherein the branches are configured to be positioned between the patient and the moisture absorbing pad and in contact with skin of the patient.

2. The device of claim 1, further comprising at least two sensing electrodes and sensing circuitry configured to sense urine leakage via the sensing electrodes.

3. The device of claim 2, wherein the sensing electrode is configured to sense wetness.

4. The device of claim 3, wherein the stimulation generator is configured to deliver stimulation in response to the sensing circuitry sensing a wetness volume above a predetermined volume.

5. The device of claim 2, wherein at least one of the sensing electrodes is within approximately 10 centimeters of at least one of the stimulation electrodes.

6. The device of claim 2, wherein at least one of the sensing electrodes is within approximately 12 centimeters of at least one of the stimulation electrodes.

7. The device of claim 1, wherein the moisture absorbing pad is disposable.

8. The device of claim 1, wherein the moisture absorbing pad comprises an adhesive configured to adhere to an undergarment.

9. The device of claim 1, wherein the lead is a spring loaded member configured to bias the stimulation electrodes against skin of the patient.

10. The device of claim 3, wherein at least a portion of the moisture absorbing pad is configured to be positioned between the patient and the sensing electrodes.

11. The device of claim 1, wherein the stimulation electrodes are spaced apart from one another to straddle a midline of a clitoris of a patient.

12. The device of claim 1, further comprising a flex circuit substrate, the stimulation generator located on the flex circuit substrate.

13. The device of claim 1, wherein the at least two stimulation electrodes are positioned to deliver the stimulation to the first dorsal genital nerve and the second dorsal genital nerve of a female patient.

* * * * *